(12) United States Patent
Xu et al.

(10) Patent No.: US 12,194,063 B2
(45) Date of Patent: Jan. 14, 2025

(54) TRADITIONAL CHINESE MEDICINE MIXTURE AND TRADITIONAL CHINESE MEDICINE EFFECTIVE INGREDIENT COMPOUND WITH FUNCTION OF PROMOTING DIRECTIONAL DIFFERENTIATION OF STEM CELLS INTO CARDIOMYOCYTES, AND APPLICATIONS THEREOF

(71) Applicant: BEIJING UNIVERSITY OF CHINESE MEDICINE, Beijing (CN)

(72) Inventors: Anlong Xu, Beijing (CN); Hongmei Li, Beijing (CN)

(73) Assignee: BEIJING UNIVERSITY OF CHINESE MEDICINE, Beijing (CN)

( * ) Notice: Subject to any disclaimer, the term of this patent is extended or adjusted under 35 U.S.C. 154(b) by 0 days.

(21) Appl. No.: 18/433,467

(22) Filed: Feb. 6, 2024

(65) Prior Publication Data

US 2024/0180973 A1    Jun. 6, 2024

Related U.S. Application Data

(63) Continuation of application No. PCT/CN2021/139375, filed on Dec. 17, 2021.

(30) Foreign Application Priority Data

Sep. 7, 2021 (CN) .......................... 202111045654.2

(51) Int. Cl.
| | | |
|---|---|---|
| *A61K 35/60* | (2006.01) | |
| *A61K 31/343* | (2006.01) | |
| *A61K 31/661* | (2006.01) | |
| *A61K 31/704* | (2006.01) | |
| *A61K 31/7048* | (2006.01) | |
| *A61K 35/30* | (2015.01) | |
| *A61K 35/32* | (2015.01) | |
| *A61K 35/50* | (2015.01) | |
| *A61K 36/258* | (2006.01) | |
| *A61K 36/28* | (2006.01) | |
| *A61K 36/296* | (2006.01) | |
| *A61K 36/424* | (2006.01) | |
| *A61K 36/481* | (2006.01) | |
| *A61K 36/537* | (2006.01) | |
| *A61K 38/02* | (2006.01) | |
| *A61K 38/18* | (2006.01) | |
| *A61P 9/00* | (2006.01) | |

(52) U.S. Cl.
CPC ............ *A61K 35/60* (2013.01); *A61K 31/343* (2013.01); *A61K 31/661* (2013.01); *A61K 31/704* (2013.01); *A61K 31/7048* (2013.01); *A61K 35/30* (2013.01); *A61K 35/32* (2013.01); *A61K 35/50* (2013.01); *A61K 36/258* (2013.01); *A61K 36/28* (2013.01); *A61K 36/296* (2013.01); *A61K 36/424* (2013.01); *A61K 36/481* (2013.01); *A61K 36/537* (2013.01); *A61K 38/02* (2013.01); *A61K 38/18* (2013.01); *A61P 9/00* (2018.01); *A61K 2236/15* (2013.01); *A61K 2236/19* (2013.01); *A61K 2236/53* (2013.01)

(58) Field of Classification Search
None
See application file for complete search history.

(56) References Cited

U.S. PATENT DOCUMENTS

2020/0377859 A1    12/2020   Huang

FOREIGN PATENT DOCUMENTS

| CA | 2518508   |   | 9/2004 |
|----|-----------|---|--------|
| CN | 1091648 A | * | 9/1994 |
| CN | 1332710   |   | 8/2007 |
| CN | 103087984 |   | 5/2013 |
| CN | 104894058 |   | 9/2015 |

(Continued)

OTHER PUBLICATIONS

Seo TB, Han IS, Yoon JH, Seol IC, Kim YS, Jo HK, An JJ, Hong KE, Seo YB, Kim DH, Park SK, Yang DC, Namgung U. Growth-promoting activity of Hominis Placenta extract on regenerating sciatic nerve. Acta Pharmacol Sin. Jan. 2006;27(1):50-8. doi: 10.1111/j.1745-7254.2006.00252.x. PMID: 16364210. (Year: 2006).*

(Continued)

*Primary Examiner* — Allison M Fox
*Assistant Examiner* — Qinhua Gu
(74) *Attorney, Agent, or Firm* — JCIPRNET

(57) ABSTRACT

The invention discloses a traditional Chinese medicine mixture with a function of promoting directional differentiation of stem cells into cardiomyocytes, which comprises syngnathus, cornu cervi pantotrichum, hippocampus, ginseng, astragalus, epimedium, placenta hominis, salvia miltiorrhiza, gynostemma pentaphyllum and saussurea involucrata. The invention discloses a traditional Chinese medicine effective ingredient compound with a function of promoting directional differentiation of stem cells into cardiomyocytes. The invention further discloses a chemical compound with a function of promoting directional differentiation of stem cells into cardiomyocytes, which is a brand-new chemical compound from a mixture of velvet antler polypeptide, a syngnathus extract and a hippocampus extract—a new isomer of iridoid glycoside Scropolioside D. The invention further discloses uses of the mixture, the compound and the chemical compound in preparation of a drug or a kit for promoting directional differentiation of stem cells into cardiomyocytes and in scientific research.

4 Claims, 14 Drawing Sheets

Specification includes a Sequence Listing.

(56) References Cited

FOREIGN PATENT DOCUMENTS

| CN | 110025699 | 7/2019 |
|---|---|---|
| CN | 110157663 | 8/2019 |
| CN | 113662985 | 11/2021 |

OTHER PUBLICATIONS

Liu Q, Wen J, Peng Z, Liu F, Tong X. Review of the powder and decoction formulae in Traditional Chinese Medicine based on pharmacologically active substances and clinical evidence. J Tradit Chin Med. Jun. 2015;35(3):355-60. doi: 10.1016/s0254-6272(15)30110-2. PMID: 26237843. (Year: 2015).*

Machine translation of CN1091648A (Year: 1994).*

Chen, Jinlian et al., "Current Situation and Future Development Trend of Traditional Chinese Medicine in Cell Therapy", Drug Evaluation Research, vol. 44, No. 2, Feb. 28, 2021, with English abstract thereof, pp. 265-272.

Ji, Yanqiong et al., "Study on the pharmacological basis and mechanism of action of active ingredients in traditional Chinese medicine for anti heart failure", China Pharmacy, vol. 30, No. 3, Feb. 15, 2019, with English abstract thereof, pp. 1-7.

Liu, Hong et al., "Traditional Chinese medicine ingredients induce differentiation of stem cells into cardiomyocytes", Proceedings of the Third Symposium of Clinical Pharmacology and Toxicology Committee, Chinese Association of Integrative Medicine, 2019, Sep. 23, 2019, with English abstract thereof, pp. 1-2.

Gao, Yuecai et al., "Revealing Nourishing Kidney Drugs in the Culture and Differentiation of Stem Cells", Chinese Journal of Engineering Research, vol. 17, No. 14, Apr. 2, 2013, with English abstract thereof, pp. 2609-2616.

Xiaoling Song et al., "Study on the Effect of Single Chinese Medicine and Active Ingredients on Stem Cells in Vitro", Chinese Journal of Basic Medicine in Traditional Chinese Medicine, vol. 17. No.3, Mar. 2011, with English translation thereof, pp. 1-8.

Lili Jiang et al., "Stimulation of sphingosine-1-phosphate on cardiomyogenic differentiation of mesenchymal stem cells", Chinese Journal of Biotechnology, vol. 29, No. 11, Nov. 25, 2013, with English abstract thereof, pp. 1617-1628.

Hu, Wen-xing et al., "Evaluate the clinical curative effect of Fuyuan capsule in patients with qi deficiency and blood stasis", China Medical Herald, vol. 5, No. 12, Apr. 2008, with English abstract thereof, pp. 51-53.

"International Search Report (Form PCT/ISA/210) of PCT/CN2021/139375," mailed on May 17, 2022, with English translation thereof, pp. 1-11.

* cited by examiner

SEQUENCE LISTING

```
Sequence total quantity: 28
SEQ ID NO: 1              moltype = DNA   length = 21
FEATURE                   Location/Qualifiers
source                    1..21
                          mol_type = other DNA
                          organism = synthetic construct
SEQUENCE: 1
tttgtgggcc tgaagaaaac t                                              21

SEQ ID NO: 2              moltype = DNA   length = 21
FEATURE                   Location/Qualifiers
source                    1..21
                          mol_type = other DNA
                          organism = synthetic construct
SEQUENCE: 2
agggctgtcc tgaataagca g                                              21

SEQ ID NO: 3              moltype = DNA   length = 20
FEATURE                   Location/Qualifiers
source                    1..20
                          mol_type = other DNA
                          organism = synthetic construct
SEQUENCE: 3
ctgggttgat cctcggacct                                                20

SEQ ID NO: 4              moltype = DNA   length = 19
FEATURE                   Location/Qualifiers
source                    1..19
                          mol_type = other DNA
                          organism = synthetic construct
SEQUENCE: 4
ccatcggagt tgctctcca                                                 19

SEQ ID NO: 5              moltype = DNA   length = 20
FEATURE                   Location/Qualifiers
source                    1..20
                          mol_type = other DNA
                          organism = synthetic construct
SEQUENCE: 5
ctcgcccttc ttcaccgatg                                                20

SEQ ID NO: 6              moltype = DNA   length = 21
FEATURE                   Location/Qualifiers
source                    1..21
                          mol_type = other DNA
                          organism = synthetic construct
SEQUENCE: 6
gtaggactcg taggcgttgt a                                              21

SEQ ID NO: 7              moltype = DNA   length = 19
FEATURE                   Location/Qualifiers
source                    1..19
                          mol_type = other DNA
                          organism = synthetic construct
SEQUENCE: 7
actctcccgg cacgtagac                                                 19

SEQ ID NO: 8              moltype = DNA   length = 20
FEATURE                   Location/Qualifiers
source                    1..20
                          mol_type = other DNA
                          organism = synthetic construct
SEQUENCE: 8
agggattcga gatccgtccg                                                20

SEQ ID NO: 9              moltype = DNA   length = 21
FEATURE                   Location/Qualifiers
source                    1..21
                          mol_type = other DNA
                          organism = synthetic construct
SEQUENCE: 9
ggtgccagtt aaagatgacg c                                              21

SEQ ID NO: 10             moltype = DNA   length = 20
FEATURE                   Location/Qualifiers
source                    1..20
                          mol_type = other DNA
                          organism = synthetic construct
```

```
SEQUENCE: 10
gaggcaaaat ggtcggcaag                                                       20

SEQ ID NO: 11            moltype = DNA  length = 21
FEATURE                  Location/Qualifiers
source                   1..21
                         mol_type = other DNA
                         organism = synthetic construct
SEQUENCE: 11
gacctccaca gagaagtcga g                                                     21

SEQ ID NO: 12            moltype = DNA  length = 21
FEATURE                  Location/Qualifiers
source                   1..21
                         mol_type = other DNA
                         organism = synthetic construct
SEQUENCE: 12
tgcctttttc ttagggcaga g                                                     21

SEQ ID NO: 13            moltype = DNA  length = 21
FEATURE                  Location/Qualifiers
source                   1..21
                         mol_type = other DNA
                         organism = synthetic construct
SEQUENCE: 13
tccatcggag ccgaagaaat c                                                     21

SEQ ID NO: 14            moltype = DNA  length = 21
FEATURE                  Location/Qualifiers
source                   1..21
                         mol_type = other DNA
                         organism = synthetic construct
SEQUENCE: 14
gtgtcggtgg atcaaagcac a                                                     21

SEQ ID NO: 15            moltype = DNA  length = 21
FEATURE                  Location/Qualifiers
source                   1..21
                         mol_type = other DNA
                         organism = synthetic construct
SEQUENCE: 15
tttgaccttc gaggcaagtt t                                                     21

SEQ ID NO: 16            moltype = DNA  length = 20
FEATURE                  Location/Qualifiers
source                   1..20
                         mol_type = other DNA
                         organism = synthetic construct
SEQUENCE: 16
cccggttttc cttctcggtg                                                       20

SEQ ID NO: 17            moltype = DNA  length = 21
FEATURE                  Location/Qualifiers
source                   1..21
                         mol_type = other DNA
                         organism = synthetic construct
SEQUENCE: 17
ggaggagtcc aaaccaaagc c                                                     21

SEQ ID NO: 18            moltype = DNA  length = 23
FEATURE                  Location/Qualifiers
source                   1..23
                         mol_type = other DNA
                         organism = synthetic construct
SEQUENCE: 18
tcaaagtcca ctctctctcc atc                                                   23

SEQ ID NO: 19            moltype = DNA  length = 21
FEATURE                  Location/Qualifiers
source                   1..21
                         mol_type = other DNA
                         organism = synthetic construct
SEQUENCE: 19
gagccgaaaa gaaagcctga a                                                     21

SEQ ID NO: 20            moltype = DNA  length = 20
FEATURE                  Location/Qualifiers
source                   1..20
                         mol_type = other DNA
```

```
                    organism = synthetic construct
SEQUENCE: 20
caccgacacg tctcactcag                                               20

SEQ ID NO: 21           moltype = DNA  length = 21
FEATURE                 Location/Qualifiers
source                  1..21
                        mol_type = other DNA
                        organism = synthetic construct
SEQUENCE: 21
cgacacccca atctcgatat g                                             21

SEQ ID NO: 22           moltype = DNA  length = 21
FEATURE                 Location/Qualifiers
source                  1..21
                        mol_type = other DNA
                        organism = synthetic construct
SEQUENCE: 22
gttgcacaga tagtgacccg t                                             21

SEQ ID NO: 23           moltype = DNA  length = 22
FEATURE                 Location/Qualifiers
source                  1..22
                        mol_type = other DNA
                        organism = synthetic construct
SEQUENCE: 23
gaacgtaaca gacaggtgac at                                            22

SEQ ID NO: 24           moltype = DNA  length = 19
FEATURE                 Location/Qualifiers
source                  1..19
                        mol_type = other DNA
                        organism = synthetic construct
SEQUENCE: 24
cggctcgttg tactccgtg                                                19

SEQ ID NO: 25           moltype = DNA  length = 19
FEATURE                 Location/Qualifiers
source                  1..19
                        mol_type = other DNA
                        organism = synthetic construct
SEQUENCE: 25
ggtgactgga gcgccttag                                                19

SEQ ID NO: 26           moltype = DNA  length = 20
FEATURE                 Location/Qualifiers
source                  1..20
                        mol_type = other DNA
                        organism = synthetic construct
SEQUENCE: 26
gcgcacatga gagattggga                                               20

SEQ ID NO: 27           moltype = DNA  length = 21
FEATURE                 Location/Qualifiers
source                  1..21
                        mol_type = other DNA
                        organism = synthetic construct
SEQUENCE: 27
ggagcgagat ccctccaaaa t                                             21

SEQ ID NO: 28           moltype = DNA  length = 23
FEATURE                 Location/Qualifiers
source                  1..23
                        mol_type = other DNA
                        organism = synthetic construct
SEQUENCE: 28
ggctgttgtc atacttctca tgg                                           23
```

TRADITIONAL CHINESE MEDICINE MIXTURE AND TRADITIONAL CHINESE MEDICINE EFFECTIVE INGREDIENT COMPOUND WITH FUNCTION OF PROMOTING DIRECTIONAL DIFFERENTIATION OF STEM CELLS INTO CARDIOMYOCYTES, AND APPLICATIONS THEREOF

CROSS-REFERENCE TO RELATED APPLICATION

This application is a continuation of international application of PCT application Ser. No. PCT/CN2021/139375, filed on Dec. 17, 2021, which claims the priority benefit of China application no. 202111045654.2, filed on Sep. 7, 2021. The entirety of each of the above-mentioned patent applications is hereby incorporated by reference herein and made a part of this specification.

REFERENCE TO A SEQUENCE LISTING

The instant application contains a Sequencing Listing which has been submitted electronically in XML format and is hereby incorporated by reference in its entirety. Said XML copy, created on Feb. 5, 2024, is named 142904_SEQUENCELISTING and is 25,877 bytes in size.

BACKGROUND OF THE INVENTION

1. Technical Field

The present invention relates to the technical field of stem cells, and particularly to a traditional Chinese medicine mixture, a traditional Chinese medicine effective ingredient compound and a chemical compound, and applications thereof.

2. Background Art

In recent years, the cardiological community has made great progress in drug research and surgical treatment, but heart failure is still a main cause of death worldwide. Even with the rapid maturity and popularization and application of cardiac intervention technology, there are still inevitable myocardial ischemia reperfusion injury and irreversible myocardial necrosis after myocardial infarction, which still affect the functional recovery of heart to varying degrees. Especially for patients suffering from end-stage heart failure who are drug-resistant due to long-term drug therapy, the only optional treatment means is heart transplantation, but many factors such as a high transplantation cost, a lack of heart donors and postoperative immune rejection seriously hinder the wide application of the heart transplantation in clinic. Therefore, how to find a new treatment means to protect or even repair damaged myocardium to the maximum extent except for conventional drug treatment and surgical treatment has become a hot and difficult point in the field of heart treatment.

A key link of formation of chronic heart failure refers to dysfunction after cardiomyocyte injury, myocardial fibrosis and ventricular remodeling until functional decompensation, but cardiomyocytes of a mature individual are terminally differentiated cells, which rarely have a regenerative capacity so as to be difficult to meet the need of repairing damaged myocardium, and cannot replace and supplement seriously lost cells during heart failure. With the rapid development of stem cell research and regenerative medicine, the repair of damaged tissues and organs by a stem cell-related technical means to restore normal structures and functions of the tissues and organs has become a new round of medical technology revolution after drug treatment and surgical treatment, which really raises a disease prevention and treatment model to a level of "manufacturing and regeneration". In recent years, people began to explore the transplantation of different types of stem cells in vivo to improve a heart function, wherein the stem cells comprise embryonic stem cells, hematopoietic stem cells, bone marrow mesenchymal stem cells, endothelial progenitor cells, skeletal muscle stem cells and induced pluripotent stem cells. However, ideal cell types and most effective transplantation methods are still unknown.

There is a treatment method with many advantages, which refers to reprogramming self-derived somatic cells into iPS cells, and then directionally inducing the iPS cells into cardiomyocytes for transplantation. Because these cells are autologous, a potential immune rejection risk and an ethical controversy of cell transplantation can be completely avoided. Existing researches show that, when beating cardiomyocytes directionally induced from the iPS are orthotopically injected into injured myocardium, not only teratoma formation is avoided, but also the heart function is improved to varying degrees and an area of infarcted myocardium is reduced, showing exciting repair potential.

Although the cardiomyocytes induced from the iPS in vitro have a precise curative effect on the repair of damaged myocardium, there are still challenges, and how to preserve and survive transplanted cells in a harsh micro-environment of a myocardial infarction area for a long time and how to obtain a huge number of cells needed for transplantation are the most discussed topics in the community. Currently reported clinical researches on small samples show that the transplantation of cardiomyocytes into patients suffering from heart failure after myocardial infarction can only improve a short-term heart function, but long-term follow-up results are not ideal, which may be because that continuous myocardial ischemia and hypoxia and inflammatory reaction lead to a change of myocardial micro-environment, so that transplanted cardiomyocytes have a low survival rate and are extremely easy to apoptosis, and cardiomyocytes in a tissue injury area have a small survival amount, thus having a direct impact on a transplantation treatment effect. It is estimated that an average number of human myocardial tissues lost after myocardial infarction needs at least $1\times10^9$ cardiomyocytes to compensate, but there are large technical difficulty and workload to obtain such a large number of cardiomyocytes by in-vitro induced differentiation. There is also evidence showing that the cardiomyocytes induced from the iPS do not fully have morphological and functional characteristics of mature cardiomyocytes, and a potential arrhythmia complication and a long-term unstable therapeutic effect after transplantation have become main obstacles to clinical application.

To sum up, there is an urgent need for an induction drug capable of promoting directional differentiation of stem cells into high-purity and functionally mature cardiomyocytes.

SUMMARY OF THE INVENTION

One object of the present invention is to solve at least the above problems and/or defects, and to provide at least the advantages that will be described hereinafter.

Another object of the present invention is to provide a traditional Chinese medicine mixture with a function of promoting directional differentiation of stem cells into cardiomyocytes.

Another object of the present invention is to provide a traditional Chinese medicine effective ingredient compound with a function of promoting directional differentiation of stem cells into cardiomyocytes.

Another object of the present invention is to provide a chemical compound with a function of promoting directional differentiation of stem cells into cardiomyocytes.

Yet another object of the present invention is to provide uses of the traditional Chinese medicine mixture, the traditional Chinese medicine effective ingredient compound and/or the chemical compound in preparation of a drug or a kit for promoting directional differentiation of stem cells into cardiomyocytes and in scientific research.

Therefore, the present invention provides technical solutions as follows.

A traditional Chinese medicine mixture with a function of promoting directional differentiation of stem cells into cardiomyocytes is provided, which comprises: syngnathus, cornu cervi pantotrichum, hippocampus, ginseng, astragalus, epimedium, placenta hominis, salvia miltiorrhiza, gynostemma pentaphyllum and saussurea involucrata.

Preferably, in the traditional Chinese medicine mixture with the function of promoting directional differentiation of stem cells into cardiomyocytes, the syngnathus, the cornu cervi pantotrichum, the hippocampus, the ginseng, the astragalus, the epimedium, the placenta hominis, the salvia miltiorrhiza, the gynostemma pentaphyllum and the saussurea involucrata all have the same mass.

Preferably, in the traditional Chinese medicine mixture with the function of promoting directional differentiation of stem cells into cardiomyocytes, the syngnathus, the cornu cervi pantotrichum, the hippocampus, the ginseng, the astragalus, the epimedium, the placenta hominis, the salvia miltiorrhiza, the gynostemma pentaphyllum and the saussurea involucrata all adopt corresponding traditional Chinese medicine powders.

Preferably, in the traditional Chinese medicine mixture with the function of promoting directional differentiation of stem cells into cardiomyocytes, various traditional Chinese medicine powders comprising a syngnathus powder, a cornu cervi pantotrichum powder, a hippocampus powder, a ginseng powder, an astragalus powder, an epimedium powder, a placenta hominis powder, a salvia miltiorrhiza powder, a gynostemma pentaphyllum powder and a saussurea involucrata powder are respectively dissolved in DMSO to be prepared into stock solutions for use.

Drug analysis is carried out on the traditional Chinese medicine mixture with the function of promoting directional differentiation of stem cells into cardiomyocytes by a liquid chromatography-mass spectrometry method, and according to the present invention, monomer ingredients capable of promoting directional differentiation of stem cells into cardiomyocytes are acquired:

A traditional Chinese medicine effective ingredient compound with a function of promoting directional differentiation of stem cells into cardiomyocytes is provided, which comprises icariin, astragaloside, ginsenoside Rg1, PLGF2, salvianolic acid B, sphingosine-1-phosphate, velvet antler polypeptide, a syngnathus extract and a hippocampus extract.

A chemical compound with a function of promoting directional differentiation of stem cells into cardiomyocytes is provided, wherein the chemical compound is a brand-new chemical compound obtained by carrying out drug analysis on the traditional Chinese medicine mixture with the function of promoting directional differentiation of stem cells into cardiomyocytes by the liquid chromatography-mass spectrometry method, and is a brand-new chemical compound newly discovered from a mixture of the velvet antler polypeptide, the syngnathus extract and the hippocampus extract, the chemical compound is a new isomer of iridoid glycoside Scropolioside D, and a molecular formula of the chemical compound is $C_{34}H_{42}O_{17}$, with a structure as follows:

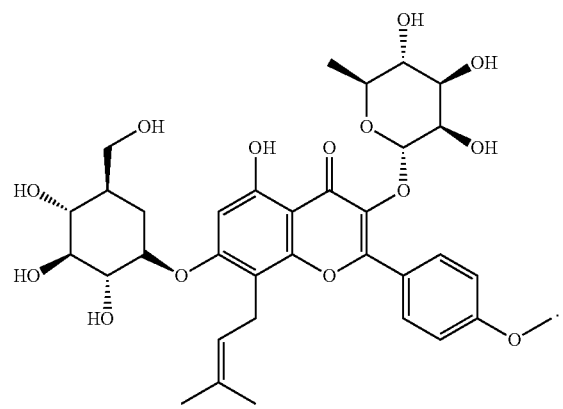

Uses of the traditional Chinese medicine mixture, the traditional Chinese medicine effective ingredient compound and/or the chemical compound in preparation of a drug or a kit for promoting directional differentiation of stem cells into cardiomyocytes and in scientific research are provided.

The present invention comprises at least the following beneficial effects.

According to the present invention, essence replenishment and heart nourishment are taken as a basic idea, and a composition formula of traditional Chinese medicines with essence replenishment and qi benefiting is selected to uniquely prepare the traditional Chinese medicine mixture Mix in the present invention for optimized induction of stem cell-derived cardiomyocytes (hiPS-CMs). According to the present invention, the traditional Chinese medicine mixture at the optimal ratio is added in a mesoderm stage, a cardiac mesoderm stage and a cardiac progenitor cell stage, it is found that the traditional Chinese medicine mixture is added in a whole process from an initial stage of mesoderm formation to differentiation and maturation of cardiac progenitor cells, and the traditional Chinese medicine mixture is removed in a maintenance and culture stage of cardiomyocytes, so that mature spontaneously beating cardiomyocytes with a differentiation rate 3 times higher than that of a standard induction scheme may be rapidly and stably differentiated, thus successfully establishing an optimized scheme for traditional Chinese medicine-assisted induction of the hiPS-CMs. The optimized scheme has important advantages that there is no need for co-culture with exogenous supporting cells (such as endoderm-like cells), good repeatability is achieved, the differentiated cardiomyocytes have high purity and maturity, and myofilaments and myomeres are clear and complete.

According to the present invention, effective ingredients are further extracted from the traditional Chinese medicine mixture Mix, and the traditional Chinese medicine effective ingredient Compound is independently developed and added into an iPS differentiation system, so that the hiPS-CMs with a high differentiation rate and high sensitivity are successfully established, which provides an ideal in-vitro experimental model for drug metabolism, toxicity detection and new drug development, and is also an optimal tool for developing etiological research of major and difficult heart diseases in the future. In addition, a stable electrophysiological function and a mature ultra micro-structure of the hiPS-CMs optimally induced by the traditional Chinese medicine Compound have great therapeutic potential in repairing damaged myocardium by in-vivo transplantation treatment, and may provide brand-new therapeutic idea and method for clinical prevention and treatment of chronic heart diseases, thus having broad promotion and application prospects.

Other advantages, objects and features of the present invention will be partially reflected by the following description, and will be partially understood by those skilled in the art through researching and practicing the present invention.

DETAILED DESCRIPTION OF THE EMBODIMENTS

Figure 1:
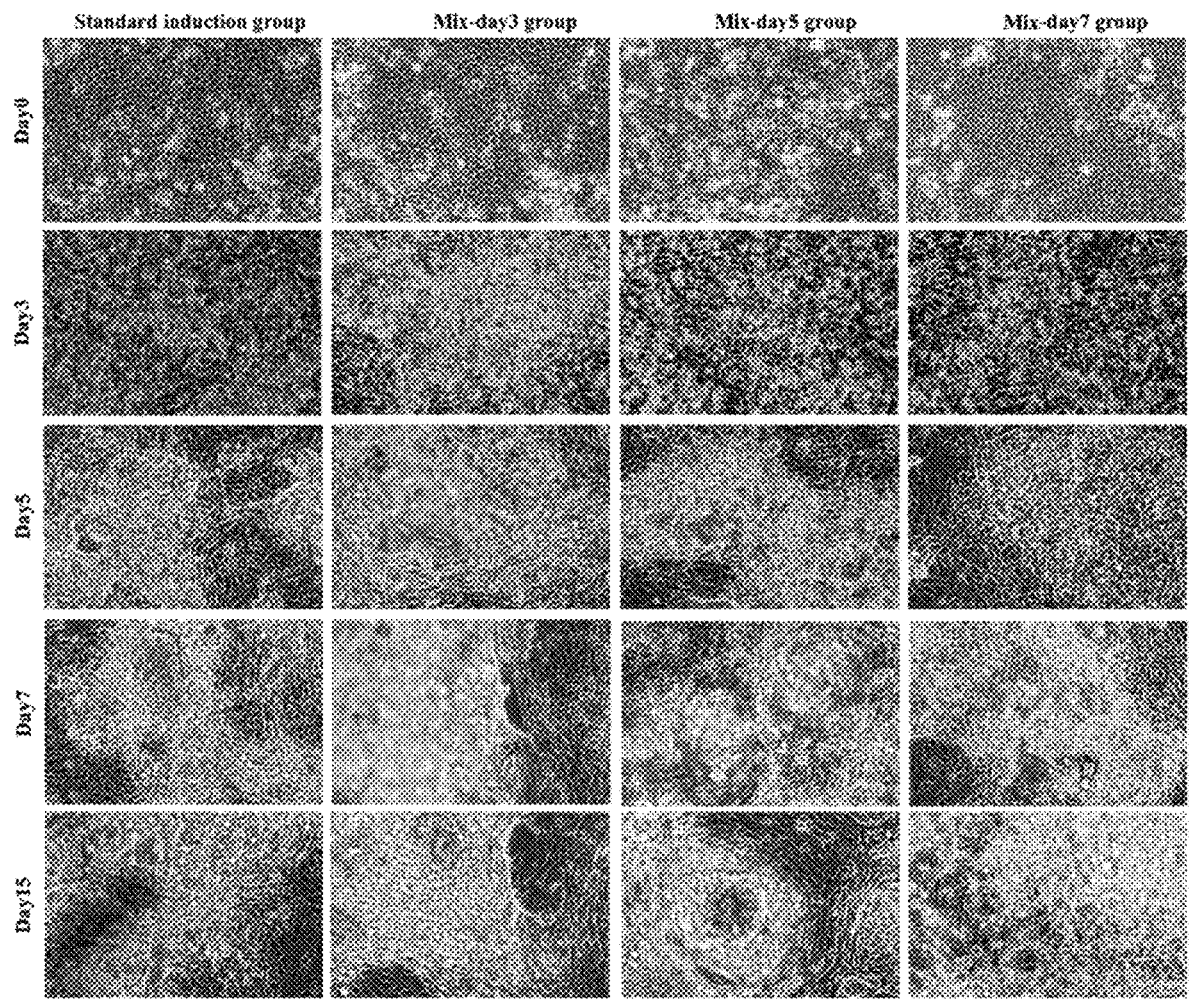
FIG. 1 is an image of characteristic deformation (x20) of iPS-differentiated cardiomyocytes under traditional Chinese medicine mixture Mix-assisted induction according to the present invention at different time points.

The present invention is further described in detail hereinafter with reference to the drawings, so that those skilled in the art can implement according to the specification.

It should be understood that the terms such as "have", "contain" and "comprise" used herein do not indicate the existence or addition of one or more other elements or combinations thereof.

The present invention provides a traditional Chinese medicine mixture with a function of promoting directional differentiation of stem cells into cardiomyocytes, which comprises syngnathus, cornu cervi pantotrichum, hippocampus, ginseng, astragalus, epimedium, placenta hominis, salvia miltiorrhiza, gynostemma pentaphyllum and saussurea involucrata.

In some embodiments of the present invention, preferably, in the traditional Chinese medicine mixture, the syngnathus, the cornu cervi pantotrichum, the hippocampus, the ginseng, the astragalus, the epimedium, the placenta hominis, the salvia miltiorrhiza, the gynostemma pentaphyllum and the saussurea involucrata all have the same mass.

In some embodiments of the present invention, preferably, the syngnathus, the cornu cervi pantotrichum, the hippocampus, the ginseng, the astragalus, the epimedium, the placenta hominis, the salvia miltiorrhiza, the gynostemma pentaphyllum and the saussurea involucrata all adopt corresponding traditional Chinese medicine powders.

In some embodiments of the present invention, preferably, various traditional Chinese medicine powders comprising a syngnathus powder, a cornu cervi pantotrichum powder, a hippocampus powder, a ginseng powder, an astragalus powder, an epimedium powder, a placenta hominis powder, a salvia miltiorrhiza powder, a gynostemma pentaphyllum powder and a saussurea involucrata powder are respectively dissolved in DMSO to be prepared into stock solutions for use.

Drug analysis is carried out on the traditional Chinese medicine mixture with the function of promoting directional differentiation of stem cells into cardiomyocytes by a liquid chromatography-mass spectrometry method, and according to the present invention, monomer ingredients capable of promoting directional differentiation of stem cells into cardiomyocytes are acquired. Therefore, the present invention further discloses a traditional Chinese medicine effective ingredient compound with a function of promoting directional differentiation of stem cells into cardiomyocytes, which comprises icariin, astragaloside, ginsenoside Rg1, PLGF2, salvianolic acid B, sphingosine-1-phosphate, velvet antler polypeptide, a syngnathus extract and a hippocampus extract.

In some embodiments of the present invention, preferably, a preparation method of the syngnathus extract comprises: drying the syngnathus, then cutting and pulverizing the dried syngnathus, and sieving the pulverized syngnathus with an 80-mesh sieve for later use; weighing 2 parts of syngnathus powder, decocting one part with water, heating and refluxing the decocting solution to retract for 3 times, and combining the three extracting solutions for later use; refluxing and extracting the other part with 75% ethanol for 3 times, and combining the three extracting solutions for later use; adding protease into residues after water extraction and alcohol extraction for hydrolysis, then carrying out enzyme deactivation, and filtering the mixture with 350-mesh filter cloth to obtain a filtrate for later use; and mixing the water extracting solution, the alcohol extracting solution and the enzymolysis solution, and subjecting the mixture to low-temperature vacuum concentration, filtration, spray drying, pulverization, mixing, sieving and packaging to obtain the syngnathus extract.

A preparation method of the hippocampus extract comprises: drying and then cutting and pulverizing the hippocampus, and sieving the hippocampus powder with an 80-mesh sieve for later use. Weighing 2 parts of hippocampus powder, decocting one part with water, heating and refluxing the decocting solution to retract for 3 times, and combining the three extracting solutions for later use; refluxing and extracting the other part with 75% ethanol for 3 times, and combining the three extracting solutions for later use; adding protease into residues after water extraction and alcohol extraction for hydrolysis, then carrying out enzyme deactivation, and filtering the mixture with 350-mesh filter cloth to obtain a filtrate for later use; and mixing the water extracting solution, the alcohol extracting solution and the enzymolysis solution, and subjecting the mixture to low-temperature vacuum concentration, filtration, spray drying, pulverization, mixing, sieving and packaging to obtain the hippocampus extract.

The present invention further provides a chemical compound with a function of promoting directional differentiation of stem cells into cardiomyocytes, wherein the chemical compound is a brand-new chemical compound obtained by carrying out drug analysis on the traditional Chinese medicine mixture with the function of promoting directional differentiation of stem cells into cardiomyocytes by the liquid chromatography-mass spectrometry method, and the chemical compound is from a mixture of the velvet antler polypeptide, the syngnathus extract and the hippocampus extract, the chemical compound is a new isomer of iridoid glycoside Scropolioside D, and a molecular formula of the chemical compound is $C_{34}H_{42}O_{17}$, with a structure as follows:

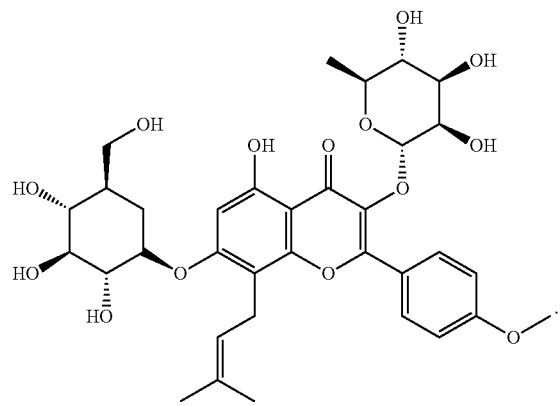

The present invention further provides uses of the traditional Chinese medicine mixture, the traditional Chinese medicine effective ingredient compound and/or the chemical compound in preparation of a drug or a kit for promoting directional differentiation of stem cells into cardiomyocytes and in scientific research.

In order to make those skilled in the art better understand the technical solutions of the present invention, the following embodiments are now provided for description.

Reagents used in the present invention:

TABLE 1

List of antibodies used in immunofluorescence detection

| Target | Host | Supplier | Cat no. | Dilution |
|---|---|---|---|---|
| SMA | Rabbit | Proteintech | 55135-1-AP | 1:200 |
| Cyto C | Mouse | Proteintech | 66264-1-Ig | 1:100 |
| c-TNI | Rabbit | Abcam | Ab52802 | 1:200 |
| Donkey anti-Rabbit IgG Alexa Fluor 488 | Donkey | Invitrogen | A21206 | 1:200 |
| Donkey anti-Rabbit IgG Alexa Fluor 647 | Donkey | Invitrogen | A31573 | 1:200 |

SMA: smooth muscle actin; Cyto C: Cytochrome C; c-TNI: cardiac Troponin I.

Matrigel matrix gel, purchased from BD company in the United States, with function of promoting cell adhesion.

Trizol lysate (company: Invitrogen, model: 15596-026).

DMEM sugar-free culture medium (company: GIBCO, article number: 11966-025).

Y27632 factor, apoptosis inhibitor, purchased from SIGMA Company in the United States, with function of inhibiting apoptosis.

E8 stem cell culture medium, purchased from StemCell Company in the United States, with function of maintenance culture of iPS cells.

mTeSR stem cell culture medium, purchased from StemCell Company in the United States, with function of multiplication culture of iPS cells.

CHIR99021, small molecule differentiation inducing agent, purchased from SIGMA Company in the United States, with function of inducing differentiation of iPS into mesoderm. CDM culture medium, adopting RPMI 1640 culture medium purchased from GIBCO Company in the United States, with function of serving as solvent for differentiating culture medium.

Pen/Strep, streptomycin, purchased from GIBCO Company in the United States, with antibacterial function.

MEM NEAA, non-essential amino acid solution, purchased from GIBCO Company in the United States, with function of serving as cell culture additive.

Bovine serum albumin BSA, purchased from SIGMA Company in the United States, with function of serving as cell culture additive.

AA2P ascorbic acid, purchased from SIGMA Company in the United States, with function of serving as cell differentiation solution additive.

MTG thioglycerol, purchased from SIGMA Company in the United States, with function of serving as cell differentiation solution additive, for current use after current preparation.

bFGF human alkaline fibroblast growth factor, purchased from Pepro Tech Company in the United States, with function of inducing further differentiation of iPS into mesoderm.

IWP2, Wnt inhibitor, purchased from SIGMA Company in the United States, with function of inducing differentiation of iPS into cardiac mesoderm.

KOSR, serum substitute, purchased from GIBCO Company in the United States, with function of cell culture additive.

Cyto C primary antibody, cytochrome C antibody, purchased from Proteintech Company, with article number: 66264-1-Ig.

I. Experimental Research on Differentiation of Hips Into Cardiomyocytes Under Optimized Induction by Saponin+ Traditional Chinese Medicine Mixture Mix:

① Preparation Method (1) 10 mL of DMSO was added into 1 g of syngnathus powder to prepare 100 mg/mL stock solution; 10 mL of DMSO was added into 1 g of cornu cervi pantotrichum powder to prepare 100 mg/mL stock solution; 5 mL of DMSO was added into 0.5 g of hippocampus powder to prepare 100 mg/mL stock solution; 10 mL of DMSO was added into 1 g of ginseng powder to prepare 100 mg/mL stock solution; 10 mL of DMSO was added into 1 g of astragalus powder to prepare 100 mg/mL stock solution; 10 mL of DMSO was added into 1 g of epimedium powder to prepare 100 mg/mL stock solution; 10 mL of DMSO was added into 1 g of placenta hominis powder to prepare 100 mg/mL stock solution; 10 mL of DMSO was added into 1 g of salvia miltiorrhiza powder to prepare 100 mg/mL stock solution; 10 mL of DMSO was added into 1 g of gynostemma pentaphyllum powder to prepare 100 mg/mL stock solution; and 10 mL of DMSO was added into 1 g of saussurea involucrata powder to prepare 100 mg/mL stock solution.

(2) 1 mL of each of the above stock solutions was taken to be fully mixed (10 mL in total), and added into a corresponding culture medium at a ratio of 10:1000 for

TABLE 2

Sequence information of primers for Q-PCR detection

| Name | Forward primer sequence | SEQ ID NO: | Reverse primer sequence | SEQ ID NO: |
|---|---|---|---|---|
| Human-Nanog | TTTGTGGGCCTGAAGAAAACT | 1 | AGGGCTGTCCTGAATAAGCAG | 2 |
| Human-Oct3/4 (POU5F1) | CTGGGTTGATCCTCGGACCT | 3 | CCATCGGAGTTGCTCTCCA | 4 |
| Human-Fgf4 | CTCGCCCTTCTTCACCGATG | 5 | GTAGGACTCGTAGGCGTTGTA | 6 |
| Human-Esg1 | ACTCTCCCGGCACGTAGAC | 7 | AGGGATTCGAGATCCGTCCG | 8 |
| Human-Dppa2 | GGTGCCAGTTAAAGATGACGC | 9 | GAGGCAAAATGGTCGGCAAG | 10 |
| Human-Dppa4 | GACCTCCACAGAGAAGTCGAG | 11 | TGCCTTTTTCTTAGGGCAGAG | 12 |
| Human-actinin (ACTN1) | TCCATCGGAGCCGAAGAAATC | 13 | GTGTCGGTGGATCAAAGCACA | 14 |
| Human-cTNI | TTTGACCTTCGAGGCAAGTTT | 15 | CCCGGTTTTCCTTCTCGGTG | 16 |
| Human-TNNT2 | GGAGGAGTCCAAACCAAAGCC | 17 | TCAAAGTCCACTCTCTCTCCATC | 18 |
| Human-Nkx2.5 | GAGCCGAAAAGAAAGCCTGAA | 19 | CACCGACACGTCTCACTCAG | 20 |
| Human-GATA4 | CGACACCCCAATCTCGATATG | 21 | GTTGCACAGATAGTGACCCGT | 22 |
| Human-MEF2C | GAACGTAACAGACAGGTGACAT | 23 | CGGCTCGTTGTACTCCGTG | 24 |
| Human-CX43 (GJA1) | GGTGACTGGAGCGCCTTAG | 25 | GCGCACATGAGAGATTGGGA | 26 |
| Human-GAPDH | GGAGCGAGATCCCTCCAAAAT | 27 | GGCTGTTGTCATACTTCTCATGG | 28 | intervention, that was, 10 μL of traditional Chinese medicine Mix was added into 1 mL of culture medium.

②  Experimental Flow and Results:

In this section, based on the theoretical basis of cardiac embryonic development and previous research methods, a standard induction scheme capable of realizing stable differentiation into beating cardiomyocytes was explored and integrated, and the Saponin+traditional Chinese medicine mixture Mix uniquely prepared by our team was applied at different time nodes (a mesoderm formation stage, a cardiac mesoderm formation stage and a cardiac progenitor cell formation stage) in differentiation of iPS into cardiomyocytes, so as to establish an optimized scheme for directional differentiation into cardiomyocytes under traditional Chinese medicine-assisted induction, which had high differentiation rate and maturity.

On the basis of the optimized standard scheme for directional differentiation of iPS into cardiomyocytes, the Saponin[+] traditional Chinese medicine mixture Mix uniquely prepared by our team was applied, and Q-PCR and flow cytometry were comprehensively used for detection, so as to explore an optimal intervention time node of the Saponin[+] traditional Chinese medicine mixture Mix.

(1) Experimental Grouping:

In this experiment, an intervention effect of the Saponin+ traditional Chinese medicine mixture was explored at three key time points in a process of differentiating iPS into cardiomyocytes, wherein the three key time points referred to a 3rd day of differentiation (the mesoderm formation stage), a 5th day of differentiation (the cardiac mesoderm formation stage) and a 7th day of differentiation (the cardiac progenitor cell formation stage), and there were a total of four groups: 1) standard induction group without traditional Chinese medicine; 2) Mix-day3 synergistic induction group; 3) Mix-day5 synergistic induction group; and 4) Mix-day7 synergistic induction group.

(2) Experimental Operation:

1) iPS cells continuously passaged for at least five generations were inoculated in a six-well plate pre-laid with Matrigel matrix gel by a density of 2×10$^6$ cells/mL, 2 mL of E8 stem cell culture medium containing 10 μM factor Y27632 was added into each well overnight, liquid replacement was carried out with an mTeSR stem cell culture medium without containing the Y27632 the next day, and then liquid replacement was carried out once a day.

2) When a density of the iPS cells in the six-well plate reached 100% and the iPS cells just covered a monolayer, directional differentiation into cardiomyocytes started to be carried out for 15 consecutive days. On a 1st day of differentiation, the mTeSR stem cell culture medium was sucked out and discarded, and the cells were washed with a DPBS buffer solution for 3 times and then suck-dried, and added with a CDM culture medium (RPMI 1640 culture medium) containing 10 μM CHIR99021 small molecule differentiation inducing agent, Pen/Strep, MEM NEAA, BSA, AA2P and MTG. On a 2nd day of differentiation, the CHIR99021-CDM culture medium was sucked out and discarded, the cells were washed with a DPBS buffer for 3 times and then suck-dried, and added with a CDM culture medium containing 5 ng/ml small molecule bFGF. On a 3rd day of differentiation, the bFGF-CDM culture medium was sucked out and discarded, the cells were washed with a DPBS buffer solution for 3 times and then suck-dried, and 1% traditional Chinese medicine mixture Mix was added into the CDM culture medium in the Mix-day3 synergistic induction group, while the traditional Chinese medicine mixture Mix was not added in the rest Mix induction groups. On a 4th day of differentiation, a half of former CDM culture medium was sucked out and discarded, a half of CDM culture medium containing 5 μM small molecule IWP2 was added, and 1% traditional Chinese medicine mixture needed to be added in the Mix-day3 synergistic induction group, while the traditional Chinese medicine mixture was not added in the rest Mix induction groups. On a 5th day of differentiation, 1% traditional Chinese medicine mixture was added into the former culture medium in the Mix-day5 synergistic induction group, while the traditional Chinese medicine mixture was not added in the rest Mix induction groups. On a 6th day of differentiation, the IWP2-CDM culture medium was sucked out and discarded, the cells were washed with a DPBS buffer solution for 3 times and then suck-dried, and added with fresh CDM culture medium, and 1% traditional Chinese medicine mixture needed to be continuously added in the Mix-day3 and Mix-day5 synergistic induction groups, while the traditional Chinese medicine mixture was not added in the Mix-day7 synergistic induction group. On a 7th day of differentiation, a half of CDM culture medium was sucked out and discarded, a half of RPMI-1640 culture medium containing 3% KOSR was added, and 1% traditional Chinese medicine mixture was added in all three Mix synergistic induction groups. Subsequently, liquid replacement was carried out once every three days according to the same formula until the cardiomyocytes matured on a 15th day of differentiation.

3) Cell morphology changes of the iPS cells at the key time points in various groups were observed and representative images were collected, and the cardiomyocytes on the 15$^{th}$ day of differentiation were collected for specific marker gene detection, comprising undifferentiated stem cell markers (Nanog, Oct3/4 (POU5F1), Fgf4 (fibroblast growth factor 4), Esg1, Dppa2 (developmental pluripotency related gene 2), and Dppa4 (developmental pluripotency related gene 4)) and cardiac specific markers (c-TnI (cardiac troponin), TNNT-2 (skeletal muscle troponin T-2), Nkx2.5, GATA4 (GATA binding protein-4), CX43 (GJA1, connexin-3), and Mef2C (myocyte enhancer factor 2C). The optimal intervention node of the traditional Chinese medicine mixture was found by comparing beating states of the cardiomyocytes. A specific operation method was as follows: ① Extraction of total RNA: 1 mL of Trizol lysate was added into each well for cell lysis and then the mixture was centrifuged at 4° C. and 10,000 rpm for 10 minutes, the supernatant was transferred into an RNase-free centrifugal tube, 0.2 mL of chloroform was added into each tube, and the mixture was vigorously shaken for 15 seconds and then incubated at room temperature for 5 minutes. The mixture was centrifuged at 4° C. for 15 minutes, a water phase part of the sample was taken, added with 70% ethanol at 1x volume, and then transferred into an adsorption column to be centrifuged for 50 seconds, and the waste liquid was discarded. 500 μL of deproteinized liquid was added and then centrifuged for 50 seconds, and the waste liquid was discarded. 700 μL of rinsing liquid was added and then centrifuged for 1 minute, and the waste liquid was discarded. 500 μL of rinsing liquid was added and then centrifuged for 1 minute, and the waste liquid was discarded. According to an expected RNA yield, 50 μL of RNase-free water was added to a middle part of an adsorption membrane and then centrifuged for 1 minute, and the eluate was taken for later use. ② Determination of purity and concentration of total RNA: 2 μL of RNA was taken and added with 98 μL of RNase-free water, and RNA purity of A260/A280 detection was determined with an ultraviolet spectrophotometer. A concentration of total RNA (μg/μL) was calculated: A260× dilution multiple was 50×40/1,000. ③ Design and dilution of primer: the primer was synthesized by Beijing Oligobio Biological Company, and GAPDH was used as an internal reference. ④ Reverse transcription: 1 μg of RNA was taken and added with RNase-free water to prepare 9.5 μL of reaction system A, which reacted at 70° C. for 10 minutes in a reverse transcription instrument; and 2 μL of dNTP, 0.5 μL of Rnasin, 4 μL of MgCl$_2$, 1 μL of AMV, 2 μL of 10×Buffer and 1 μL of OligdT were mixed for 10 minutes, then added into the reaction system A, gently centrifuged to a tube bottom, and placed in the reverse transcription instrument to be reversely transcribed into cDNA at 42° C. for 60 minutes→at 95° °C.for 5 minutes→at 4° °C.for 5 minutes. ⑤) Real-time fluorescence PCR amplification: the cDNA was added with 80 μL of RNase-free water to be diluted by 5 times, then added with 2 μL of upstream and downstream mixed primers, 10 μL of diluted cDNA and 13 μL of PCR Mix, and mixed evenly, and then the amplification was carried out in an RNA instrument at 95° C. for 10 minutes, at 95° C. for 30 seconds, at 55° C. for 1 minute and at 72° C. for 1 minute for a total of 40 cycles. ⑥ Data processing: an expression quantity multiple of to-be-tested genes in the intervention group relative to to-be-tested genes in the blank control group was represented by $2^{-\Delta\Delta Ct}$.

4) Cardiomyocyte differentiation rates of the standard induction group and the optimal Mix induction group (a proportion of c-TNI-labeled cardiomyocytes referred to the cardiomyocyte differentiation rate) were detected by the flow cytometry, and an optimized scheme for directional differentiation of iPS into cardiomyocytes under traditional Chinese medicine mixture Mix-assisted induction with good stability and repeatability was finally integrated and formed. A specific operation method for detecting the cardiomyocyte differentiation rate by the flow cytometry was as follows: ① cells in the standard induction group and the Mix induction group on the 15th day of differentiation were dissociated and collected, and prepared into a single-cell suspension; ② the single-cell suspension was centrifuged at 350 g for 5 minutes to collect cells, and the culture medium was discarded; ③ 2 mL of DPBS buffer solution was added to resuspend the cells, and the cell suspension was centrifuged at 500 g for 5 minutes to collect cells; ④ the cells were counted, and then 100 μL of the cell suspension at a concentration adjusted to be 1×10$^7$ was taken out, added with an antibody directly labeled with c-TNI, and incubated at 4° C. in the dark for 30 minutes; ⑤ 2 mL of DPBS buffer solution was added, gently blown by 1 mL tip and evenly mixed, then the cell suspension was centrifuged at 500 g for 5 minutes, and the supernatant was discarded; ⑥ the cell suspension was centrifuged at 350 g for 5 minutes to collect cells, and the culture medium was discarded; and ⑦ 500 μL of DPBS buffer solution was added, and the cell suspension was detected by the flow cytometry.

2.2.3 Statistical Processing

A homogeneity test of variance was carried out on experimental data of various groups by SPSS 24.0 statistical software, overall means of multiple samples were compared by one-way analysis of variance, all data were expressed by mean±standard deviation (X̄±S), and statistical results showed that differences were statistically significant when $P<0.05$.

Exploration (Preferred Intervention Nodes of Traditional Chinese Medicine) and Research Results of Optimized Scheme for Differentiation of iPS into Cardiomyocytes:

Various experimental groups were all differentiated synchronously at 100% initial density, and on a 3rd day of differentiation, the Mix-day3 synergistic induction group showed obvious cell proliferation compared with other experimental groups, and cells gathered towards a center and squeezed and covered with each other. On a 5th day of differentiation, cells in the Mix-day3 synergistic induction group further proliferated rapidly, cells in the Mix-day5 synergistic induction group also proliferated slightly and stacked, and cells in the other two groups did not proliferate obviously. On a 7th day of differentiation, the cells in the Mix-day3 and Mix-day5 groups proliferated significantly, and the cells in the standard induction group and the Mix-day7 synergistic induction group also proliferated to a certain number and aggregated, but there was still a difference compared with the Mix-day3 and Mix-day5 groups. On a 15th day of differentiation, the cells in various groups could be seen to beat confluently, but there was a large difference in beating frequency. The cells in the Mix-day3 synergistic induction group started to beat for the first time on the 7th day of differentiation, and contracted and beat strongly at a frequency of 98 times/min after the 15th day of differentiation, and the beating was synchronous in all visual fields and orderly in rhythm. The cells in the Mix-day5 synergistic induction group started to beat for the first time on an 8th day of differentiation, and beat at a frequency of 90 times/minute, the beating in all areas had the same frequency, and no beating was seen in some areas. The cells in the Mix-day7 synergistic induction group and the standard induction group started to beat for the first time on a 10th day of differentiation at a similar beating amplitude and a beating frequency of about 80 times/min, and no beating was seen in some areas (FIG. 1). Based on observation of cell state in a bright field, the Mix-day3 synergistic induction group and the Mix-day5 synergistic induction group were both optional, wherein the former was the most preferred.

Figure 2:
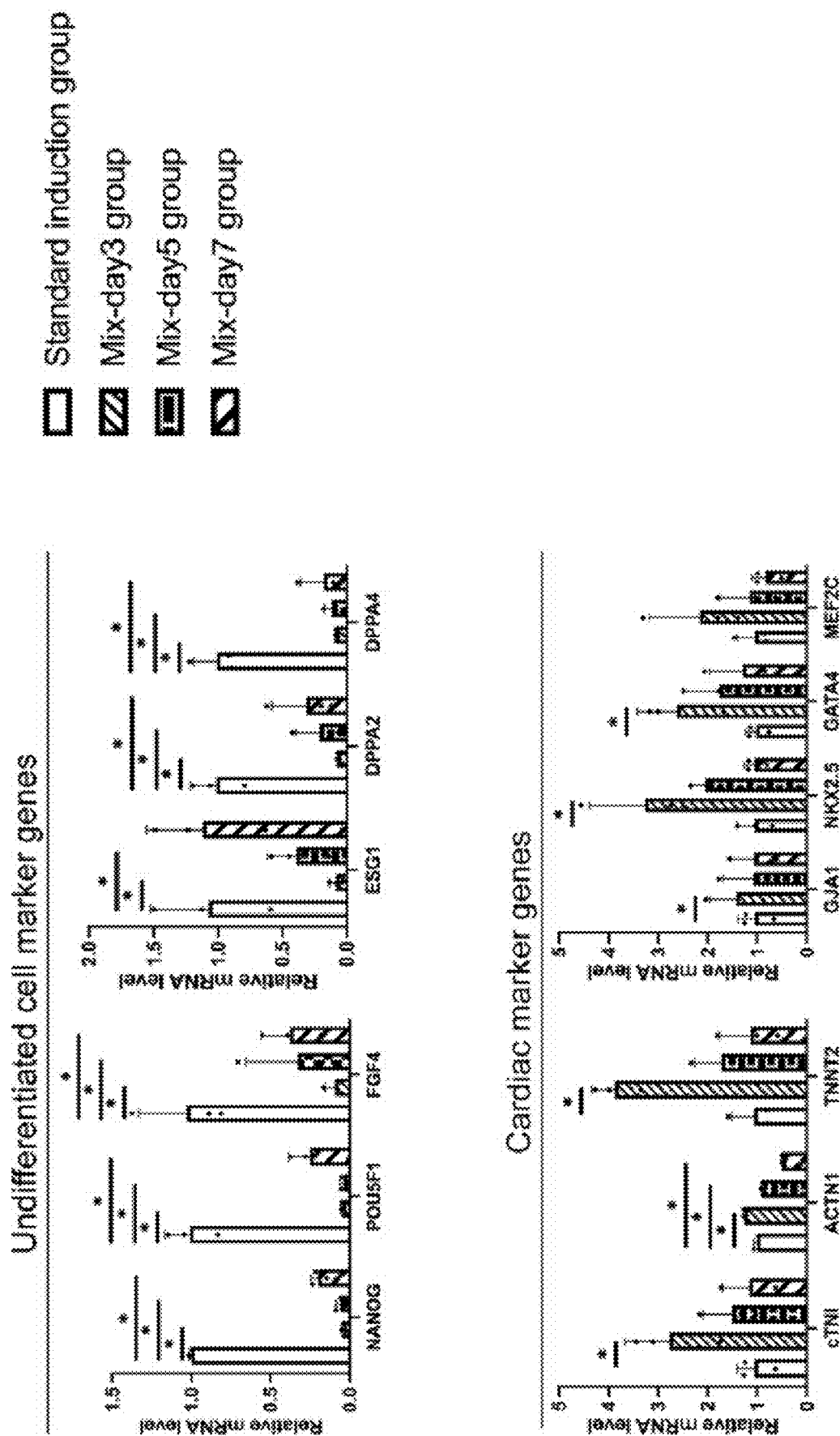
FIG. 2 is a graph showing influences of the traditional Chinese medicine mixture Mix-assisted induction at different time points on gene expression of hiPS-CMs (note: compared with a standard induction group, differences are statistically significant, *P<0.05).

Furthermore, according to the present invention, Q-PCR detection was carried out on the cells on the 15th day of differentiation, and it was found that mRNA expressions of undifferentiated stem cell-specific marker genes (Nanog, Oct3/4 (POU5F1), Fgf4, Esg1, Dppa2 and Dppa4) in the Mix-day3 synergistic induction group were significantly lower than those in other groups (*P<0.05). On the contrary, mRNA expressions of mature cardiomyocyte-specific marker genes (c-TNI, α-actinin (ACTN1), TNNT-2, CX43 (GJA1), Nkx2.5, GATA4 and Mef2C) in the Mix-day3 synergistic induction group were higher than those in other groups (*P<0.05). Therefore, according to the present invention, the 3$^{rd}$ day of differentiation was determined as optimal time to start differentiation under intervened induction by the Saponin$^+$ traditional Chinese medicine mixture Mix (FIG. 2).

Figure 3:
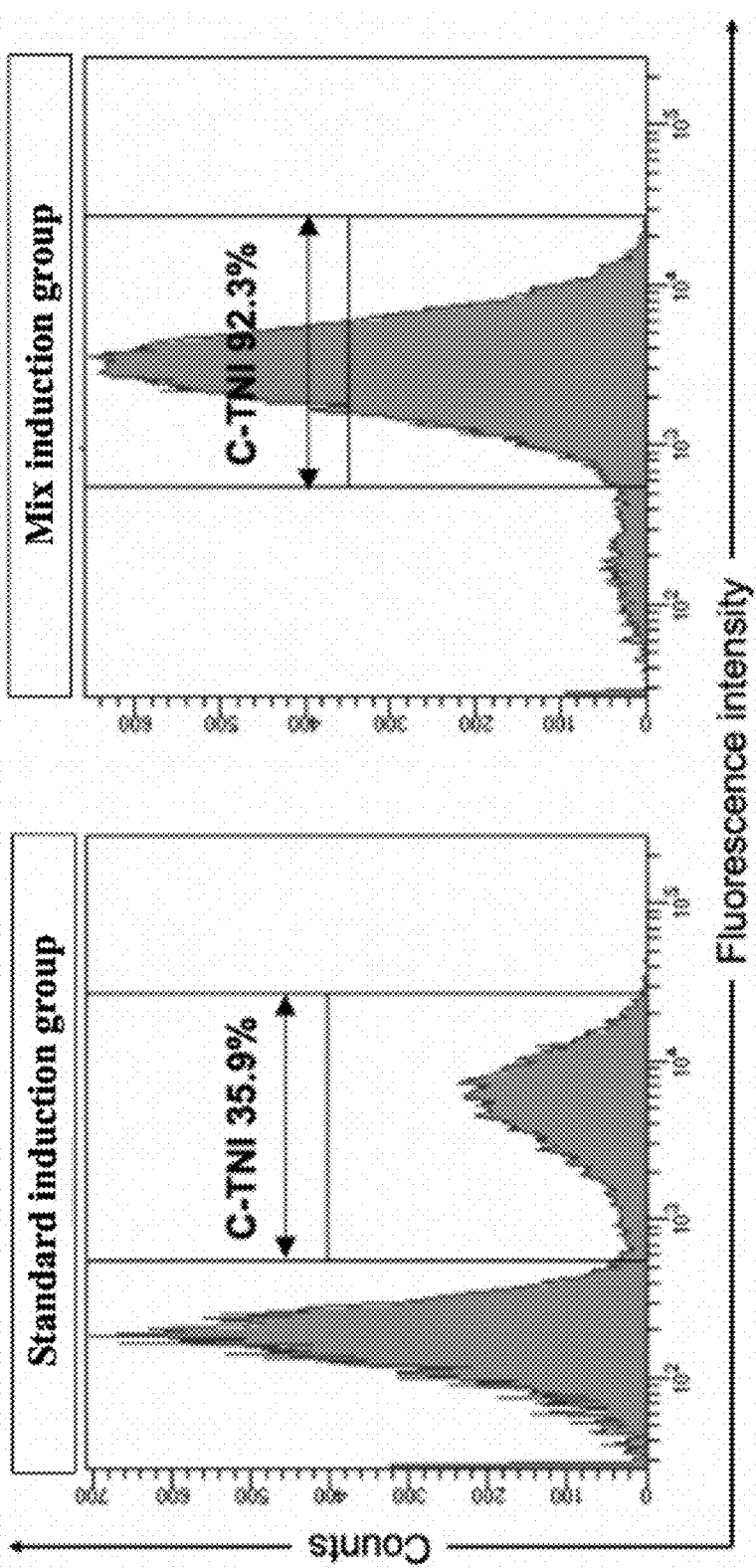
FIG. 3 is a graph showing differentiation rates of the hiPS-CMs under standard induction by flow cytometry and optimized induction by the traditional Chinese medicine mixture Mix.

After an optimal intervention node of optimized induction by the traditional Chinese medicine mixture Mix was determined, a proportion of cardiomyocytes specifically labeled with c-TNI was calculated by the flow cytometry in the present invention, so as to compare and analyze hiPS-CMs differentiation rates of a standard induction scheme and an optimized induction scheme by the traditional Chinese medicine mixture Mix. Results showed that, on the 15$^{th}$ day of differentiation, a cardiomyocyte differentiation rate of a Mix induction group was 92.3%, a cardiomyocyte differentiation rate of a standard induction group was 35.9%, and a differentiation rate of directional differentiation of iPS into cardiomyocytes under traditional Chinese medicine mixture Mix-assisted induction was 3 times that of the group without adding the traditional Chinese medicine mixture (FIG. 3).

Although an existing scheme for differentiation of iPS into cardiomyocytes had good repeatability and high differentiation stability currently, the cardiomyocyte differentiation rate was still unsatisfactory, and it was still difficult to obtain a large number of mature hiPS-CMs with high purity. In addition, according to the present invention, it was observed that after the hiPS-CMs under standard induction left a cell incubator for a period of time, a beating frequency of the hiPS-CMs was obviously reduced and rhythm of the hiPS-CMs was disordered, so that it was boldly guessed in the present invention that were arrhythmia complications caused after transplantation of the hiPS-CMs into the heart associated with not only abnormal electrical connection between transplanted cells and host's cardiomyocytes but also instability of electrical signals of the cardiomyocytes themselves transplanted into the body? Furthermore, the present invention innovatively explored the combination of traditional Chinese medicine elements into the standard induction scheme, and tried to achieve the purpose of directionally inducing cardiomyocytes with a high differentiation rate, high stability and high maturity by adding the traditional Chinese medicine mixture Mix.

It was considered in the present invention that an essence replenishment and heart nourishment method in the traditional Chinese medicine had inherent consistency with a process of forming mature cardiomyocytes by stem cell differentiation, and from an aspect of embryogenesis, stem cells basically conformed to all functional characteristics of primordial essence in the traditional Chinese medicine, and were an existence form of the primordial essence in a microscopic level of body. The primordial essence was converted into primordial qi, the primordial essence showed a substance structure, the primordial qi showed metabolism and energy transfer functions, and a process of differentiating the stem cells and forming the mature cardiomyocytes to generate energy metabolism referred to a process of converting the primordial essence into the primordial qi. Under guidance of such idea, essence replenishment and heart nourishment were taken as a basic idea in the present invention, and in combination with clinical application experience, traditional Chinese medicines with essence replenishment and qi benefiting were screened out to form the Saponin traditional Chinese medicine mixture Mix uniquely prepared by our team for the optimized induction of the hiPS-CMs. According to the present invention, a non-toxic concentration of the traditional Chinese medicine mixture Mix acting on a process of differentiating iPS cells had been preliminarily explored through a pre-experiment in an early stage, and for the next step of optimization, a fixed ratio of the traditional Chinese medicine in the present invention was researched, and intervention time points of the traditional Chinese medicine was explored in detail. The traditional Chinese medicine mixture Mix at the optimal ratio was added in a mesoderm stage, a cardiac mesoderm stage and a cardiac progenitor cell stage, it was found in the present invention that the traditional Chinese medicine mixture was added in a whole process from an initial stage of mesoderm formation to differentiation and maturation of cardiac progenitor cells, and the traditional Chinese medicine mixture Mix was removed in a maintenance and culture stage of cardiomyocytes, so that mature spontaneously beating cardiomyocytes with a differentiation rate 3 times higher than that of a standard induction scheme might be rapidly and stably differentiated, thus successfully establishing an optimized scheme for traditional Chinese medicine-assisted induction of the hiPS-CMs. The optimized scheme had important advantages that there was no need for co-culture with exogenous supporting cells (such as endoderm-like cells), good repeatability was achieved, the differentiated cardiomyocytes had high purity and maturity, and myofilaments and myomeres were clear and complete.

II. Screening and Optimization of Effective Ingredients of Saponin+ Traditional Chinese Medicine Mixture Mix— Exploratory Research on Preparation of Traditional Chinese Medicine Monomer Compound for Inducing Differentiation of hiPS into Cardiomyocytes:

Drug analysis was carried out on the Saponin+ traditional Chinese medicine Mix by a liquid chromatography-mass spectrometry method, chromatographic separation was carried out on a Waters Acquity UPLC HSS T3 column (2.1×100 mm, 1.8 μm, Milford, MA, USA), and LC was connected with a mass spectrometer through an electrospray ionization (ESI) interface. A mobile phase consisting of 0.1% formic acid (A) and ACN (B) was transported in gradient according to the following procedures: 0 minute to 15 minutes, 30% to 75% B; 15 minutes to 20 minutes, 75% to 100% B; and 20.1 minutes to 25 minutes, 30% B, a flow velocity of 0.25 mL/min. A sample introduction volume was set as 5.0 μL, a column oven was kept at 40° C., and an outlet was connected to a DAD module and IT-TOF-MS in sequence. LCMS solution software (Shimadzu Version 3) was used for data processing, and a mass tolerance calculated by a molecular weight formula was defined as ±10 ppm.

Figure 4:
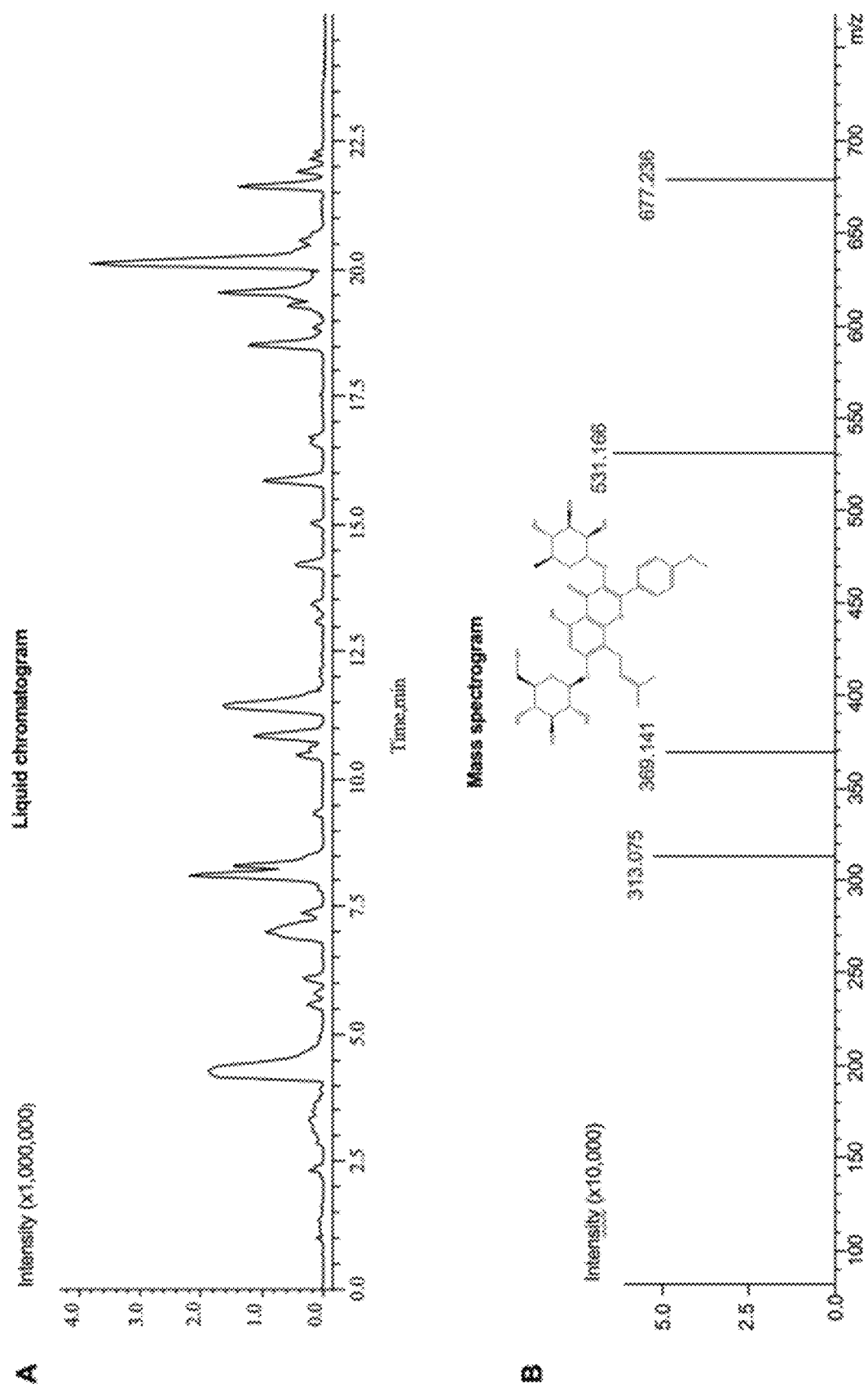
FIG. 4 is an LC-IT-TOF-MS identification graph of the traditional Chinese medicine mixture Mix according to the present invention (note: A shows a liquid chromatogram of the traditional Chinese medicine mixture Mix; and B shows a mass spectrum of the traditional Chinese medicine mixture Mix).
Figure 5:
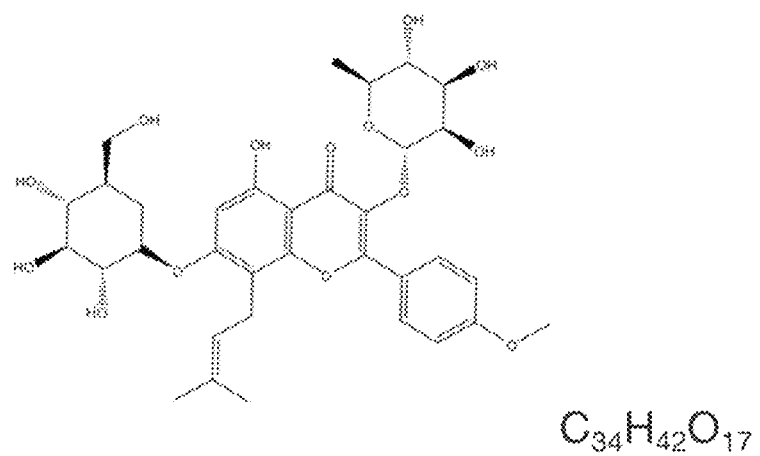
FIG. 5 is a schematic structural diagram of a chemical compound $C_{34}H_{42}O_{17}$ according to the present invention.

According to LC-IT-TOF-MS identification as shown in FIG. 4, the Saponin+traditional Chinese medicine mixture Mix comprised main monomer ingredients of icariin, astragaloside, ginsenoside Rg1, PLGF2 (recombinant human placenta growth factor-2), salvianolic acid B, sphingosine-1-phosphate, and a new isomer of iridoid glycoside Scropolioside D, and was a brand-new chemical compound, and a molecular formula of the chemical compound was $C_{34}H_{42}O_{17}$, with a structure shown in the following and FIG. 5:

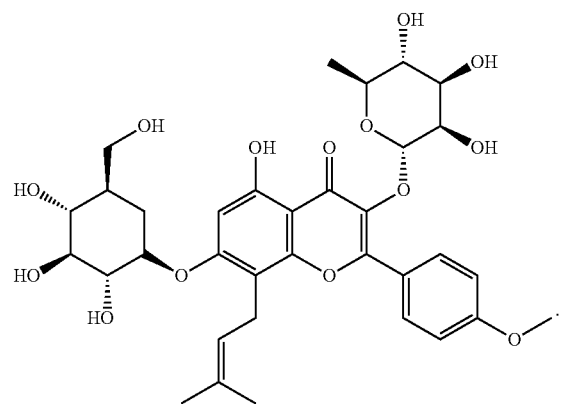

Secondary monomer ingredients were listed in the following table:

| NO. | tR | [M + H]+ | [M − H]− | [M + H]− | Formula |
| --- | --- | --- | --- | --- | --- |
| 1 | 10.863 | 376.257 | 374.243 | 420.250 | $C_{21}H_{33}N_3O_3$ |
| 2 | 11.427 | 432.235 | | | $C_{24}H_{33}NO_6$ |
| 3 | 14.235 | 496.335 | | 540.330 | $C_{26}H_{45}N_3O_6$ |
| 4 | 15.037 | 522.367 | | 566.349 | $C_{32}H_{47}N_3O_3$ |
| 5 | 15.877 | 237.136 | | | $C_{16}H_{16}N_2$ |
| 6 | 18.547 | 280.262 | | | $C_{18}H_{33}NO$ |
| 7 | 18.648 | 336.324 | | | $C_{22}H_{41}NO$ |
| 8 | 19.332 | 352.323 | | | $C_{22}H_{41}NO_2$ |

-continued

| NO. | tR | [M + H]+ | [M − H]− | [M + H]− | Formula |
|---|---|---|---|---|---|
| 9 | 19.485 | 338.343 | | | $C_{21}H_{39}NO_2$ |
| 10 | 19.555 | 256.262 | | | $C_{16}H_{33}NO$ |
| 11 | 20.130 | 282.276 | | | $C_{18}H_{35}NO$ |
| 12 | 21.632 | 284.291 | | | $C_{18}H_{37}NO$ |
| 13 | 21.924 | 310.309 | | | $C_{20}H_{39}NO$ |

On this basis, according to the present invention, composition and proportion of the Saponin+ traditional Chinese medicine mixture Mix were further optimized, and main traditional Chinese medicine monomer ingredients screened out and identified were used to replace all corresponding traditional Chinese medicine ingredients in the Mix, thus integrating the simplified traditional Chinese medicine monomer Compound. Specific preparation of the traditional Chinese medicine Compound was as follows:

20 μg/mL icariin, 20 μg/mL astragaloside, 20 μg/mL ginsenoside Rg1, 5 ng/mL PLGF$_2$, 10 μg/mL salvianolic acid B, 2 nM sphingosine-1-phosphate, 100 μg/mL velvet antler polypeptide, 100 μg/mL syngnathus extract and 100 μg/mL hippocampus extract, wherein a mixed solution of the velvet antler polypeptide, the syngnathus extract and the hippocampus extract contained a new isomer of iridoid glycoside Scropolioside D.

Figure 6:
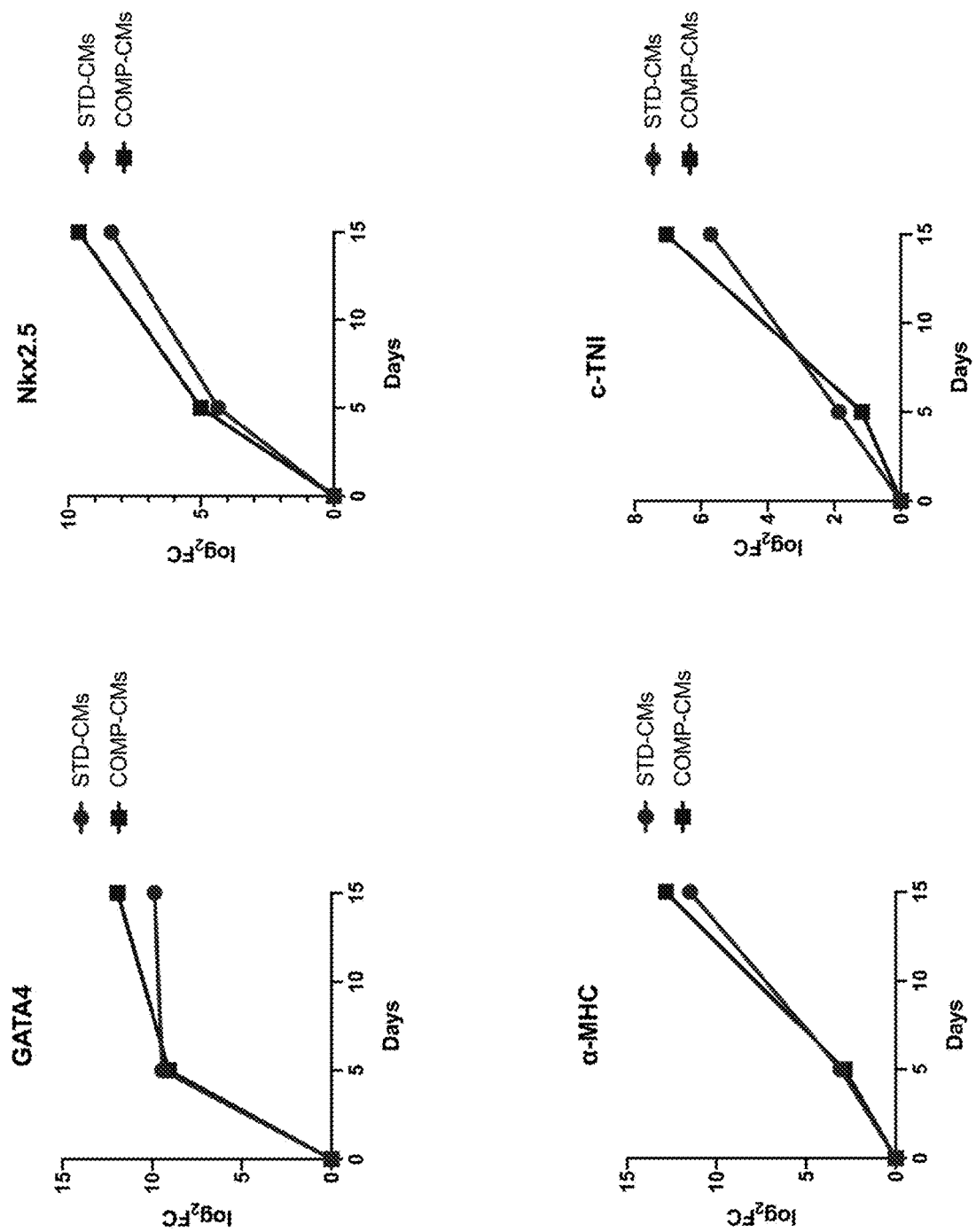
FIG. 6 shows sequencing analysis results of cell mRNA transcriptomes of the hiPS-CMs under optimized induction by a traditional Chinese medicine effective ingredient Compound and the hiPS-CMs under standard induction (without adding the traditional Chinese medicine Compound) at different differentiation time nodes (a 5th day and a 15th day of differentiation), which is a statistical chart of differentiation increases of early-stage and middle-stage maturity markers GATA4 and Nkx2.5 of cardiomyocytes and late-differentiation-stage maturity markers α-MHC and c-TNI of cardiomyocytes in a Compound induction group compared with those in the standard induction group in the present invention.

The traditional Chinese medicine Compound with the above concentrations was added in a process of directionally inducing differentiation of hiPS into cardiomyocytes, and differences and mechanisms in a gene level and a functional structure level of the hiPS-CMs obtained by standard induction (induction without adding the traditional Chinese medicine Compound) and optimized induction by the traditional Chinese medicine Compound were compared. According to the present invention, cell RNAs of hiPS on a 5th day under standard induction, on a 15th day under standard induction, on a 5th day under optimized induction by the traditional Chinese medicine Compound and on a 15th day under optimized induction by the traditional Chinese medicine Compound were extracted respectively for whole transcriptome mRNA sequencing. Results were shown in FIG. 6:

① Increases of Early-Stage and Middle-Stage Maturity Markers GATA4 and Nkx2.5 of Cardiomyocytes after Differentiation were as Follows:

it could be seen that the early-stage and middle-stage maturity markers of cardiomyocytes under optimized induction by the traditional Chinese medicine Compound started to be gradually superior to those of the standard induction group from the 5th day of differentiation, and the cardiomyocytes had a faster development and maturation speed and higher maturity.

② Increases of Late-Differentiation-Stage Maturity Markers α-MHC and c-TNI of Cardiomyocytes After Differentiation were as Follows:

it could be seen that the late-differentiation-stage maturity markers of cardiomyocytes under optimized induction by the traditional Chinese medicine Compound started to be gradually superior to those of the standard induction group from the 7th day of differentiation, and the maturity of the cardiomyocytes was much higher than that of the standard induction group on the 15th day of differentiation, showing a strong ability of the traditional Chinese medicine Compound to promote cardiomyocyte differentiation.

Furthermore, according to the present invention, an electrophysiological function of the cardiomyocytes was detected by an MEA microarray, a contraction function of the cardiomyocytes was detected by a calcium transient, a mitochondrial structure of the cardiomyocytes was detected by a mitochondrial fluorescence probe, and mitochondrial membrane potential, mitochondrial calcium and cytochrome C were detected by immunofluorescence. Structural and functional differences of the cardiomyocytes under standard induction and optimized induction by the traditional Chinese medicine Compound were compared, so that possible synergistic potential and mechanism of optimized induction by the traditional Chinese medicine Compound of the hiPS-CMs were preliminarily identified.

① Purification and Re-Inoculation of Hips-CMs Cells Under Standard Induction and Optimized Induction by Traditional Chinese Medicine Compound (1) Purification of hiPS-CMs Cells:

1) After cardiomyocyte differentiation was completed, the cardiomyocytes were purified, and a cardiomyocyte purification solution was prepared from DMEM sugar-free culture medium (company: GIBCO, article number: 11966-025)+5 mm sodium lactate.

2) After the cardiomyocytes beat stably for 1 day to 2 days, the former cardiomyocyte culture medium was sucked away, a DPBS buffer solution was added to wash the cells once, and liquid replacement was carried out with the cardiomyocyte purification solution for purification.

3) The cells were cultured in a 5% $CO_2$ incubator at a constant temperature of 37° C. for 3 days without liquid replacement in the process. After the purification was ended, a DPBS buffer solution was added to wash the cells once so as to remove dead cells, and liquid replacement was carried out with an RPMI1640 culture medium containing 3% KOSR to maintain the culture.

4) 3 days later, it could be observed that the cells resumed to beat, and cell purity was improved. According to a cell state and a purification effect, the cells could be purified by several times, until good adherence of the cells was realized and an outline of a single cell was clearly visible, so that the purification was completed.

(2) Re-Inoculation of hiPS-CMs Cells:

1) A cardiomyocyte inoculation solution was prepared from high-sugar DMEM+20% FBS+Y27632 for later use.

2) 1 mL of Matrigel matrix gel was added into a cell culture dish with an ultra-thin glass bottom, and the cell culture dish laid with the matrix gel needed to be directly placed into a cell incubator at 37° C. for 1 hour before use.

3) The differentiated cardiomyocytes were taken out, the former culture medium was sucked away, and a DPBS buffer solution was added to wash the cells once.

4) A human cardiomyocyte dissociation solution was added to completely cover the dish bottom, and the cells were incubated at 37° C. for 20 minutes. It was observed under a microscope that most of the cells were separated from each other and were "round", indicating ideal cell dissociation time. The same volume of culture medium containing serum was added to stop the dissociation, and gently blown by a pipette to prepare into a single-cell suspension, and the cell suspension was transferred into a 15 mL centrifuge tube to be centrifuged at 200 g for 5 minutes.

5) The supernatant was discarded, and the cells were resuspended with the cardiomyocyte inoculation solution, gently blown and evenly mixed, then inoculated into a glass-bottomed cell culture dish pre-laid with the matrix gel, and shaken in a horizontally crossed manner to distribute the cells evenly.

6) The cells were cultured in a 5% $CO_2$ incubator at a constant temperature of 37° C. for 24 hours, liquid replacement was carried out with an RPMI1640 culture medium containing 3% KOSR the next day, the culture was maintained until the cells were stable, and then immunofluorescence detection was carried out. Note: the cardiomyocytes temporarily stopped beating due to a passage operation and generally recovered 1 day to 3 days later.

Detection of Extracellular Electrophysiological Signal of Hips-CMs Under Standard Induction and Optimized Induction by Traditional Chinese Medicine Compound (1) A bottom of an MEA electrode plate was laid with Matrigel matrix gel one day in advance, with 5 μL for each well.

(2) The differentiated and cultured cardiomyocytes were dissociated gently the next day and then counted, and the cardiomyocytes were inoculated into the pre-coated MEA electrode plate at a density of 2×104 cells/mL per well. Before inoculation in each well, the Matrigel matrix gel pre-incubated in the well was sucked away, and 5 μL of cell suspension was carefully inoculated onto the electrode plate. It should be noted that the cell suspension was blown evenly before inoculation.

(3) After the cells were all inoculated, the electrode plate was placed into a cell incubator, taken out 4 hours to 6 hours later, and observed. At the moment, the cells started to be adherent, 300 μL of cardiomyocyte inoculation solution was replenished into each well, and the cells were cultured in the cell incubator. Liquid replacement was carried out with a cardiomyocyte culture solution containing 3% KOSR for maintenance culture the next day, and then liquid replacement was carried out every other day.

(4) 7 days after cell inoculation, after the cardiomyocytes started to beat stably, a baseline of the cardiomyocytes was detected on a computer, then 100 nM isoproterenol (ISO) was added into 2 wells of each group, 10 μM lidocaine was added into the 2 wells, and a field potential signal of the cardiomyocytes was detected 10 minutes after addition for data analysis.

③ Detection of Intracellular Calcium Transient Signal of Hips-CMs Under Standard Induction and Optimized Induction by Traditional Chinese Medicine Compound 2 μM Fluo-4 AM solution prepared from the hiPS-CMs purified and then inoculated in the glass culture dish and a HEPES buffer salt was cultured at 37° C. for 30 minutes, then a dye solution was sucked and discarded, the cells were washed with a DPBS buffer solution for 3 times, each washing lasted for 10 minutes, and spontaneous $Ca^{2+}$ transient was recorded at 37° C. by an electric inverted fluorescence microscope and a time-delay recording system in the dark. At least 6 visual fields were recorded in each culture dish, and each visual field was recorded for at least 1 minute. A magnitude of the $Ca^{2+}$ transient was represented by a change of standard fluorescence intensity, which was namely ΔF/F0, wherein F0 represented fluorescence intensity in a rest state, and background fluorescence was subtracted in all numerical calculations.

④ Detection of Mitochondrial Structure and Function of Hips-CMs Under Standard Induction and Optimized Induction by Traditional Chinese Medicine Compound (1) Detection of MTG-Labeled Mitochondrial Structure:

The culture medium of the hiPS-CMs cells purified at low density and then inoculated into the glass culture dish was replaced with a culture medium containing 100 nM MitoTracker Green (MTG) and 2 μg/mL Hoechst 33342. After being incubated in an incubator at 37° C. for 30 minutes, the cells were photographed by a confocal microscope from 6 views randomly selected, 3 samples in each of two groups of cells were imaged at high resolution, and a single mitochondrion was identified and analyzed.

(2) Fluorescence Imaging of Rhod-2 Mitochondrial Calcium:

The culture medium of the hiPS-CMs cells purified at low density and then inoculated into the glass culture dish was added with 1 μM Rhod-2/μM, and then the cells were incubated in an incubator at 37° C. for 45 minutes, and washed once with a DPBS buffer solution. Liquid replacement was carried out with a cardiomyocyte culture medium containing 5 μg/mL Hoechst 33342 and 100 nM MTG, and the cells were continuously cultured in an incubator at 37° C. for 30 minutes. Data under excitation waves of 405 nm, 488 nm and 555 nm were collected under a fluorescence microscope, fluorescence intensity of Rhod-2 was determined by Image Pro Plus software, which was compared with average fluorescence intensity of MTG-labeled mitochondria, and a ratio represented a content of the mitochondrial calcium.

(3) Fluorescence Imaging of TMRE Mitochondrial Membrane Potential:

The culture medium of the hiPS-CMs cells purified at low density and then inoculated into the glass culture dish was replaced with a culture medium containing 5 nM mitochondrial membrane potential sensitive fluorophore (TMRE), 100 nM MTG and 2 μg/mL Hoechst 33342. After being incubated in an incubator at 37° C.for 30 minutes, the cells were photographed by a fluorescence microscope from 6 views randomly selected, 3 samples in each of two groups of cells were excited at 546 nm by TMRE fluorescence, and fluorescence was collected by a 590 nm barrier filter. Fluorescence intensity of TMRE was determined by Image Pro Plus software, which was compared with average fluorescence intensity of the MTG-labeled mitochondria, and a specific value represented an average magnitude of the mitochondrial membrane potential.

(4) Immunofluorescence Imaging of Mitochondrial Cytochrome c:

1) The hiPS-CMs cells purified at low density and then inoculated into the glass culture were taken out, the culture medium in the well was discarded, the cells were gently washed with a DPBS buffer solution for 3 times, and each washing lasted for 3 minutes.

2) 1 mL of pre-cooled 4% paraformaldehyde was added into each dish, fixed at room temperature for 20 minutes, and then gently washed with a DPBS buffer solution for 3 times, and each washing lasted for 3 minutes.

3) 1 mL of PBS containing 0.2% Triton X-100 was added into each dish, stood on ice for 10 minutes, and then gently washed with a DPBS buffer solution for 3 times, and each washing lasted for 3 minutes. 4) 1 mL of PBS containing 1% BSA was added into each dish, and sealed at room temperature for 1 hour.

5) After a primary antibody of the Cyto C was diluted at a ratio of 1:100, 500 μL of the solution was taken out and dropwise added into a culture dish to make the antibody completely cover a cell surface, and incubated at 4° C. overnight.

6) The primary antibody incubation solution in the dish was sucked out, and gently washed with a DPBS buffer solution for 3 times, and each washing lasted for 3 minutes.

7) A fluorescein secondary antibody working solution prepared at 1:50 was dropwise added, and incubated at 37° C. for 30 minutes (in the dark).

8) The solution was gently washed with a DPBS buffer solution for 3 times, and each washing lasted for 3 minutes. 500 μL of DAPI staining solution was added into each well to stain at room temperature for 5 minutes.

9) The solution was gently washed with a DPBS buffer solution for 3 times, and each washing lasted for 3 minutes. A clean glass slide was taken and dropwise added with 50 µL of anti-fluorescence quenching mounting medium in a center position, the liquid was air-dried and then subjected to picture acquisition under a fluorescence microscope, and the fluorescence intensity of the Cyto C was quantitatively compared and analyzed by Image Pro Plus software.

Statistical Processing

A homogeneity test of variance was carried out on experimental data of various groups by SPSS 24.0 statistical software, overall means of multiple samples were compared by one-way analysis of variance, all data were expressed by mean±standard deviation ($\bar{X}$±S), and statistical results showed that differences were statistically significant when P<0.05.

Results

Figure 7:
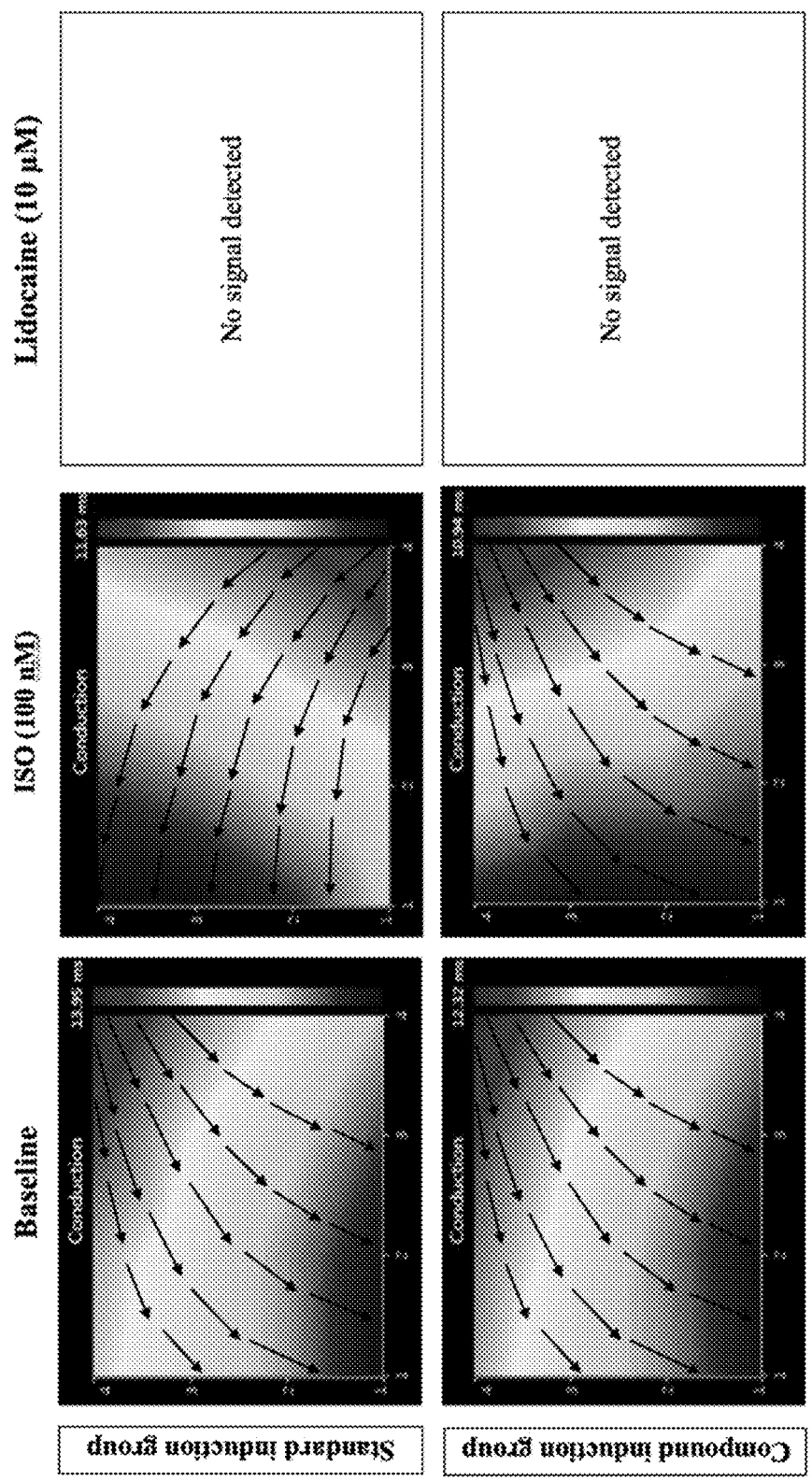
FIG. 7 is a propagation map of an electrical signal of the hiPS-CMs based on an MEA platform according to the present invention.

① Higher Electrophysiological Sensitivity and Stability of Hips-CMs Under Optimized Induction by Traditional Chinese Medicine Compound than Those Under Standard Induction According to the present invention, after the hiPS-CMs under standard induction and optimized induction by the traditional Chinese medicine Compound were purified by a sugar-free culture medium containing sodium lactate, electrophysiological functions of the hiPS-CMs processed with 100 nM isoproterenol (ISO) and 10 µM lidocaine under basic conditions were compared. Propagation of beating signals of two groups of cardiomyocytes was recorded by an MEA micro-matrix electrode system, and under basic conditions, the hiPS-CMs under standard induction and optimized induction by traditional Chinese medicine compound had similar general patterns of sequential activation of electrical signals, both of which referred to propagation from the upper right to the lower left. However, 12.32 ms was spent in completing sequential activation once by the Compound induction group, which was shorter than 13.95 ms of standard induction, showing a higher propagation speed of electrical excitation. After ISO intervention was applied, sequential activation durations of the two groups of cells were both significantly shortened. The Compound induction group was able to maintain a stable propagation direction while accelerating and strengthening the propagation of electrical signals, while the standard induction group showed an unstable change in electrical propagation compared with a reference line of the standard induction group itself, and a propagation direction of the standard induction group was reversed from the bottom right to the top left. When the lidocaine was added into the cells to inhibit electrical excitation, normal electrical propagation of the two groups of cells was interrupted, and the electrical propagation signals could not be detected, indicating that the two groups of cells had good sensitivity to an electrical excitation inhibitor (FIG. 7).

Figure 8:
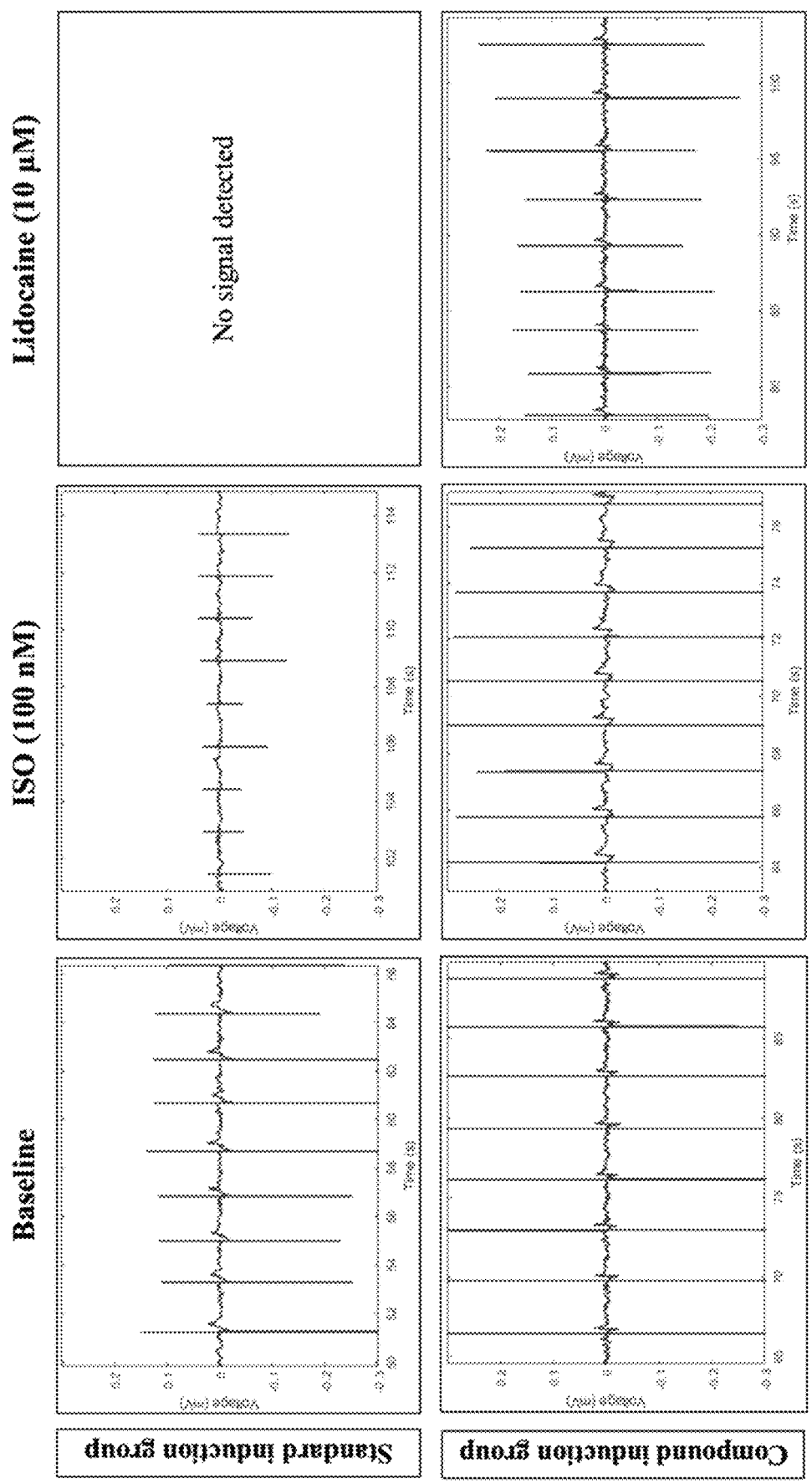
FIG. 8 is a change chart of a field potential waveform of the hiPS-CMs based on the MEA platform according to the present invention.

Similar observation results were also obtained in field potential detection of the cardiomyocytes, and it was found in the present invention that, below the reference line, the two groups of cells had uniform beating rhythm. However, the cardiomyocytes in the Compound induction group had a large and uniform beating amplitude, while the cardiomyocytes in the standard induction group had a small beating amplitude lacking synchronism in change. After ISO activation was applied, beating frequencies of the two groups of cells were both increased rapidly, wherein the beating amplitude of the standard induction group was decreased obviously and changed irregularly when the beating frequency was increased, while a myocardial contraction frequency of the Compound induction group could be increased on the basis of basically keeping the beating amplitude unchanged. When the lidocaine was applied to inhibit spontaneous beating of the two groups of cells, the beating of the hiPS-CMs in the standard induction group disappeared and no signal could be detected, while synchronous amplitude change of each beating of the hiPS-CMs in the Compound induction group could be basically maintained while slowing down the beating frequency and decreasing the beating amplitude. It could be seen that the hiPS-CMs under induction by the traditional Chinese medicine Compound had better sensitivity and tolerance to drug reaction than the standard induction group (FIG. 8).

Figure 9:
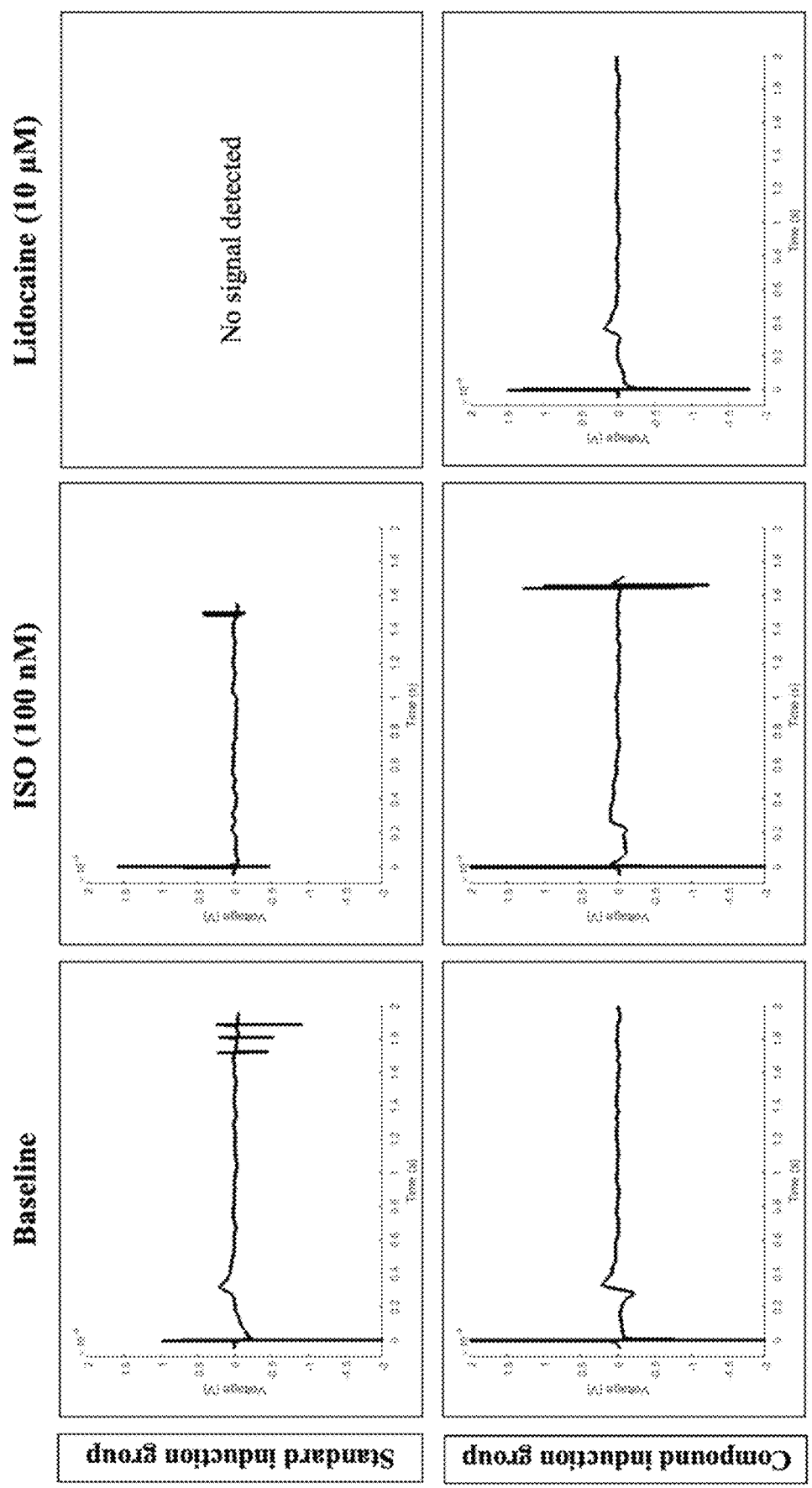
FIG. 9 is a change chart of a depolarization/repolarization time phase of the hiPS-CMs based on the MEA platform according to the present invention.

According to the present invention, a depolarization/repolarization time phase of the hiPS-CMs was further detected, and it was found that, below the reference line, depolarization and repolarization voltages of the standard induction group were lower than those of the Compound induction group, and the time phase of the standard induction group was also shorter than that of the Compound induction group. After being activated by ISO, depolarization and repolarization time of the hiPS-CMs under optimized induction by the traditional Chinese medicine Compound was obviously shortened, while the hiPS-CMs under standard induction showed disordered depolarization and repolarization processes. After contractility of the hiPS-CMs was inhibited by the lidocaine, the hiPS-CMs under optimized induction by the traditional Chinese medicine Compound could still send out a weak electrical signal to maintain a basic voltage difference, but no depolarization/repolarization signal was detected in the hiPS-CMs under standard induction (FIG. 9).

Figure 10:
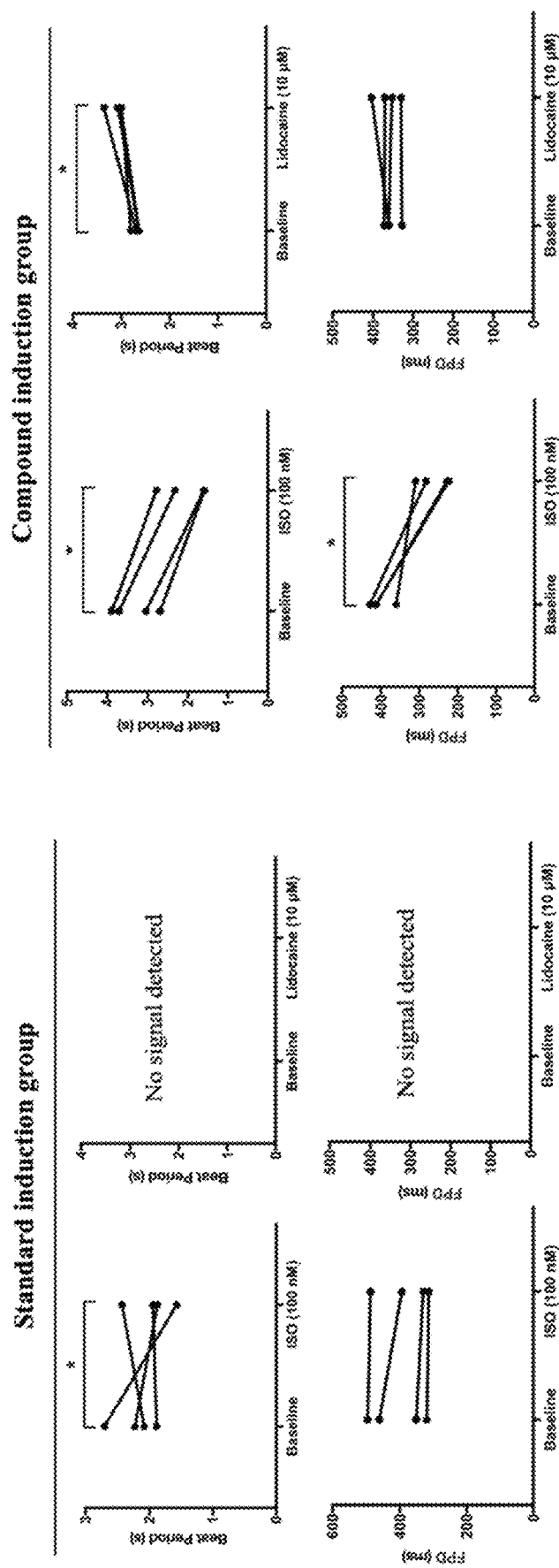
FIG. 10 is a change chart of a field potential duration of the hiPS-CMs based on the MEA platform according to the present invention (note: compared with a reference line, differences are statistically significant, *P<0.05).

In addition, according to the present invention, quantitative statistics was also carried out on field potential and depolarization/repolarization core indexes of the hiPS-CMs. Results showed that there was little difference in beating cycle between the two groups of cells under the reference line condition. However, the beating cycle of the hiPS-CMs under induction by the traditional Chinese medicine Compound was obviously shortened after the ISO intervention was applied, while the beating cycle of the hiPS-CMs under induction by the traditional Chinese medicine Compound was prolonged after the lidocaine was applied. However, such change was not obvious in the standard induction group, and activation and inhibition reactions both showed irregular and disordered change states. It was found from quantization of the depolarization/repolarization time phase in the present invention that the standard induction group was not significantly changed by the ISO intervention, and normal depolarization and repolarization processes of the hiPS-CMs under standard induction could be completely eliminated by the lidocaine, while the hiPS-CMs under optimized induction by the traditional Chinese medicine Compound could keenly perceive a positive activation effect of ISO, which significantly shortened the depolarization/repolarization time phase, and in a circumstance that the electrical activity was inhibited by the lidocaine, the depolarization/repolarization time phase could still be slightly prolonged and the basic stability of electrical activity could be ensured (FIG. 10).

Thus, it could be seen that the hiPS-CMs under optimized induction by the traditional Chinese medicine Compound had strong drug sensitivity and tolerance, and had a more mature and stable electrophysiological conduction function than the hiPS-CMs under standard induction.

Figure 11:
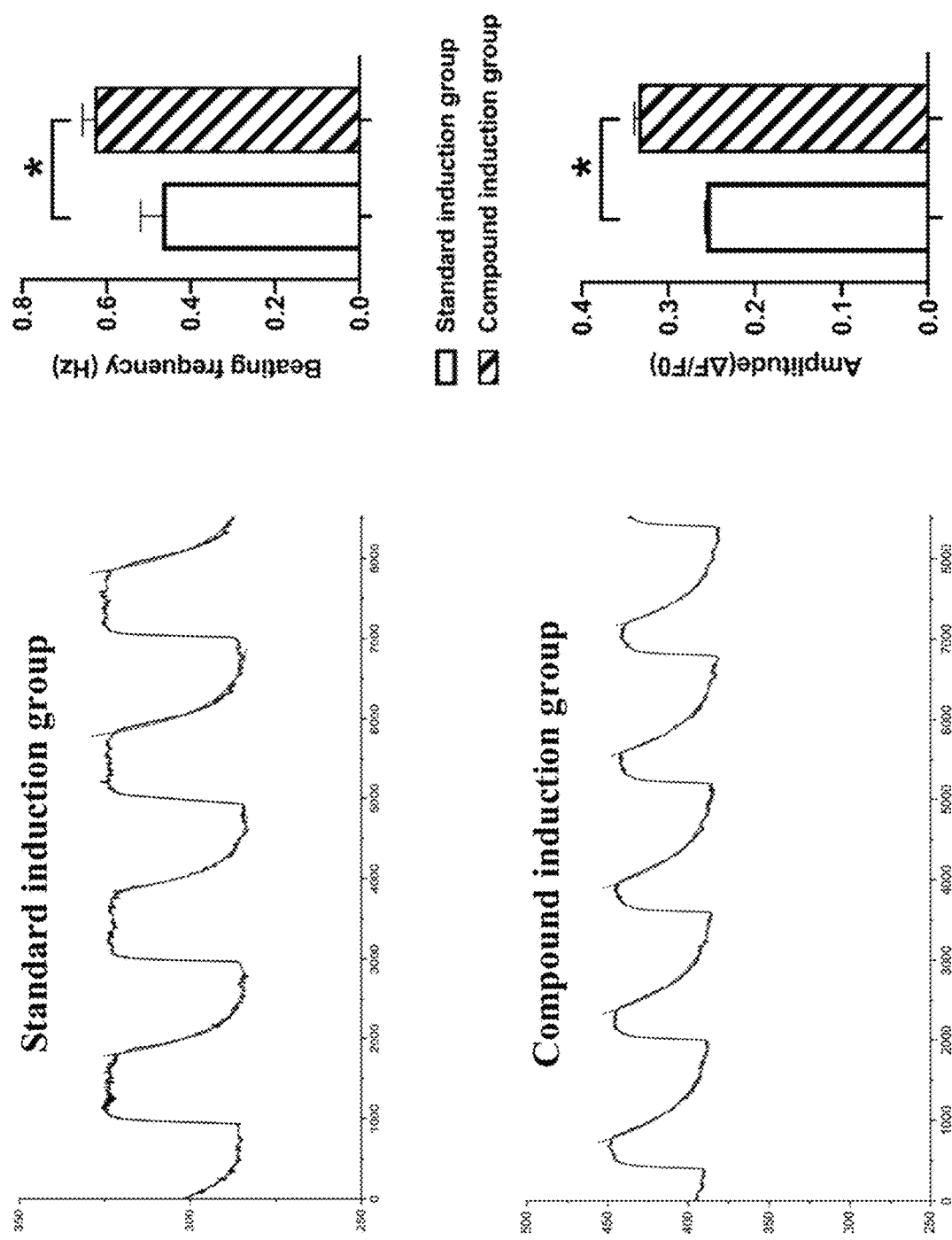
FIG. 11 is a detection diagram of a spontaneous contraction calcium transient of the hiPS-CMs according to the present invention (note: compared with the standard induction group, differences are statistically significant, *P<0.05).

② Comparison of Intracellular Calcium Transient Signals of Hips-CMs Under Standard Induction and Optimized Induction by Traditional Chinese Medicine Compound The calcium transient was a basis for contraction and relaxation reactions in a spontaneous beating process of the hiPS-CMs, and Fluo-4 was used as a marker to track a transient condition of calcium ions in the present invention (FIG. 11). ΔF/F0 represented a change proportion of fluorescence intensity after standardization. Statistical results showed that a change amplitude (ΔF/F0) of fluorescence intensity of the hiPS-CMs under optimized induction by the traditional Chinese medicine Compound at the reference line was obviously larger than that of the standard induction group without additional stimulation. Spontaneous calcium transient frequencies of the two groups of cells under basic conditions were observed, and it was found by comparing the hiPS-CMs under optimized induction by the traditional Chinese medicine Compound with the hiPS-CMs in the standard induction group that the spontaneous calcium transient frequency of the Compound induction group was significantly increased (0.63±0.03 vs.0.47±0.01, $P<0.05$, n=6).

Figure 12:
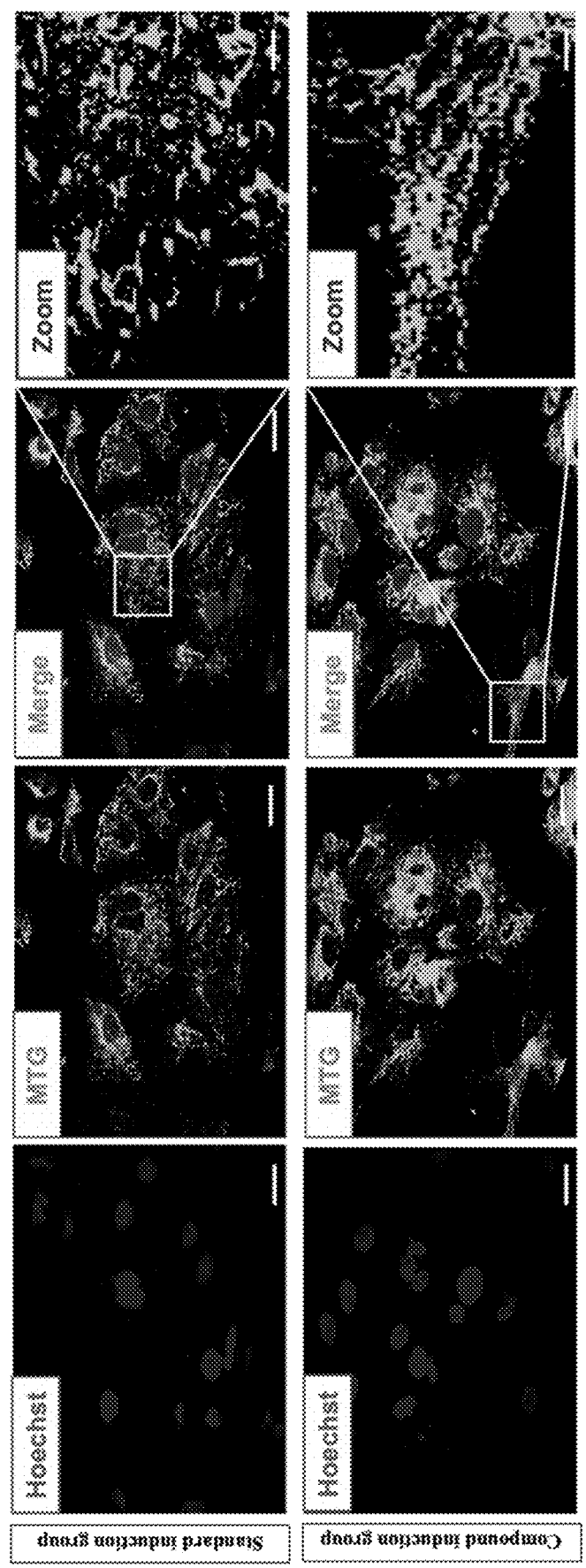
FIG. 12 is a detection diagram of a mitochondrial structure of the hiPS-CMs fluorescently-labeled with MTG according to the present invention.

③ Higher Functional Maturity of Mitochondrial Structure of Hips-CMs Under Optimized Induction by Traditional Chinese Medicine Compound than that of Standard Induction Group According to the present invention, the mitochondrial structure of the hiPS-CMs was comparatively observed by a confocal microscope, and it could be seen that mitochondria of two groups of MTG-labeled hiPS-CMs were closely distributed around nuclei. After the mitochondria were locally amplified, it was found that the mitochondria of the hiPS-CMs under standard induction were mostly short dots and rods, while the mitochondria of the hiPS-CMs under optimized induction by the traditional Chinese medicine Compound had good extension and continuity in morphology, and were filaments, long lines and reticula. The mitochondrial structure was more systematic and perfect by differentiation (FIG. 12).

Figure 13:
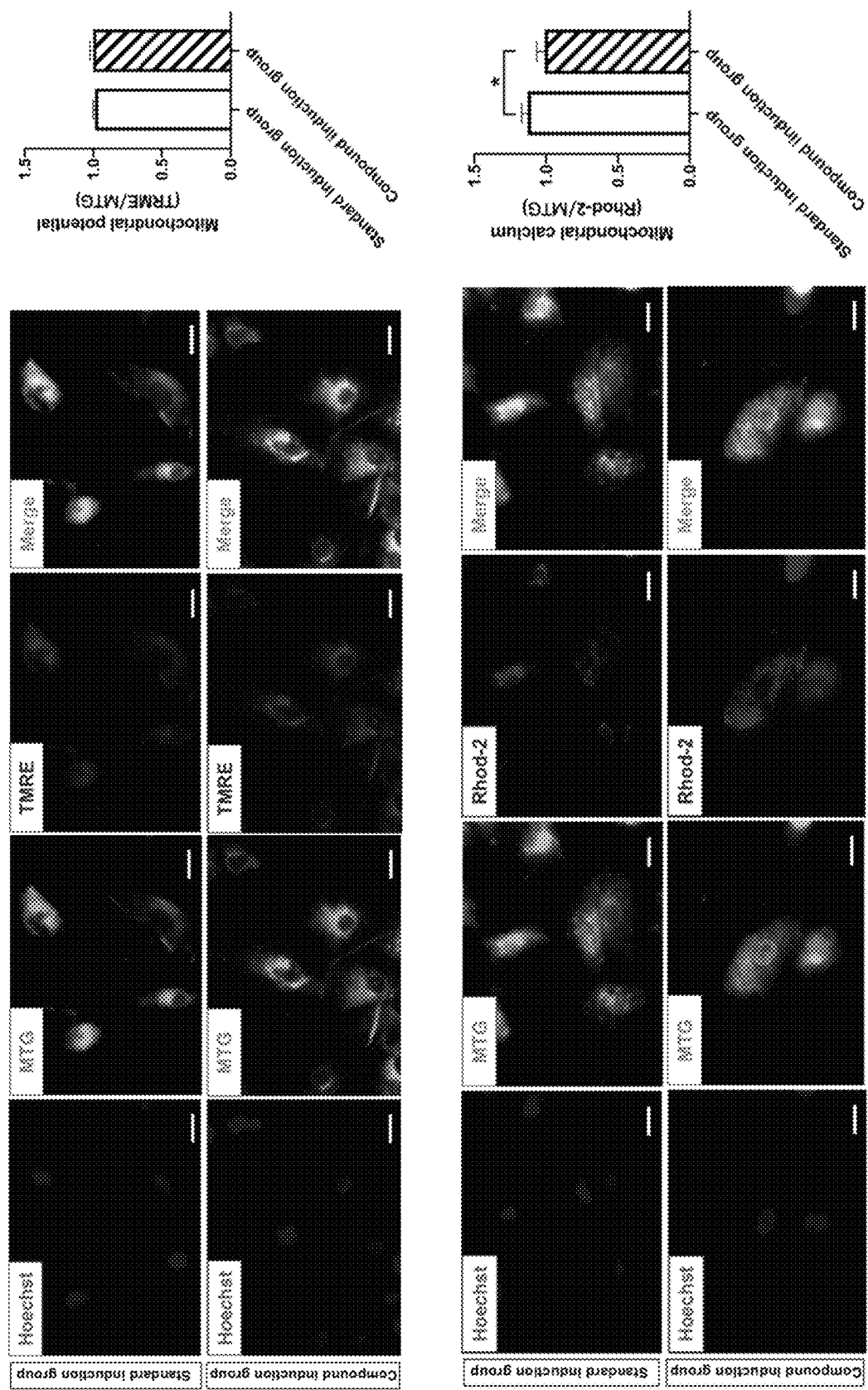
FIG. 13 is a detection diagram of mitochondrial membrane potential and mitochondrial calcium of the hiPS-CMs according to the present invention (note: compared with the standard induction group, differences are statistically significant, *P<0.05).

In order to further study a corresponding functional difference caused by a structural difference of the mitochondria of the two groups of hiPS-CMs, in the present invention, the mitochondrial membrane potential was labeled with TMRE and the mitochondrial calcium was labeled with Rhod-2, double-staining was carried out by calibration with MTG mitochondria, and fluorescence quantitative analysis was carried out after photographing by a fluorescence microscope. Results showed that, at the reference line without adding exogenous stimulation, mitochondrial membrane potentials of the hiPS-CMs in the standard induction group and the Compound induction group were equal, and there was no statistical difference in quantitative analysis of a TMRE/MTG ratio ($P>0.05$). However, mitochondrial calcium of the hiPS-CMs under optimized induction by the traditional Chinese medicine Compound was significantly lower than that of the standard induction group ($P<0.05$), and it could be seen from quantitative analysis that there was an obvious reduction trend in mitochondrial calcium accumulation of the hiPS-CMs under optimized induction by the traditional Chinese medicine Compound (FIG. 13).

Figure 14:
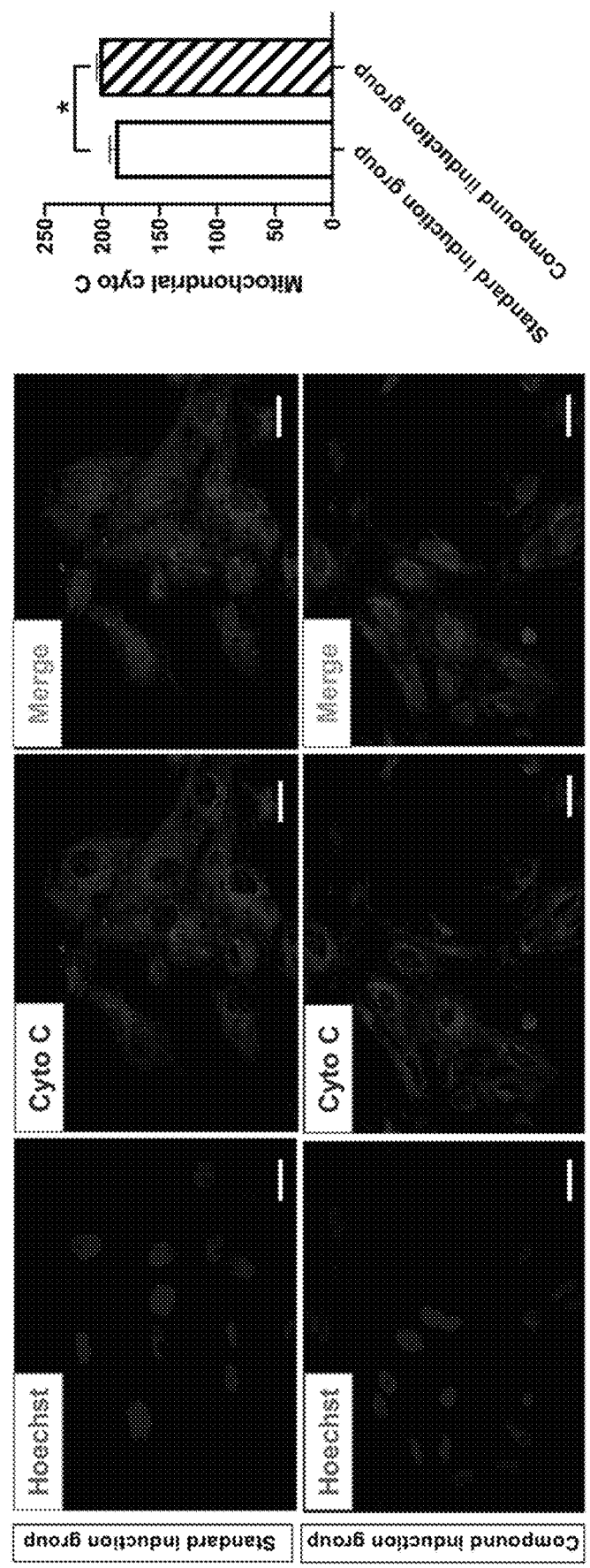
FIG. 14 is a detection diagram of mitochondrial cytochrome C of the hiPS-CMs according to the present invention (note: compared with the standard induction group, differences are statistically significant, *P<0.05).

Furthermore, the two groups of hiPS-CMs were mounted and fixed in a glass culture dish, and a content and a release condition of the cytochrome C were observed by an immunofluorescence staining method. Fluorescence quantitative analysis showed that, compared with the hiPS-CMs under standard induction, the hiPS-CMs under optimized induction by the traditional Chinese medicine Compound had higher red fluorescence intensity, and had more cytochrome C accumulated in the mitochondria ($P<0.05$), but release of the cytochrome C from the mitochondria to cytoplasm was not observed in the two groups of the hiPS-CMs (FIG. 14).

Discussion

The maturity of the cardiomyocytes comprises structural maturity and functional maturity, a sign of the structural maturity is formation of myofilaments and myomeres, and characteristics of the functional maturity are reflected in perfection of contractility, excitability and conductivity of the cardiomyocytes. With increase of differentiation maturity, the cardiomyocytes may gradually withdraw from the a cell cycle to lose proliferation ability, which gives the present invention an inspiration that: the optimized induction for directional differentiation of iPS into cardiomyocytes may have more room for expansion from a proliferation period before maturation of the cardiomyocytes. According to the present invention, in the research of the last chapter, the traditional Chinese medicine Compound independently developed by our team is subjected to assisted-induction for consecutive 8 days in an early stage of mesoderm formation, and an optimized induction scheme for the cardiomyocytes with a high differentiation rate, high purity and high stability is successfully established. In order to explore a difference in maturity of the hiPS-CMs under optimized induction by the traditional Chinese medicine Compound and standard induction, electrophysiological characteristics, subcellular structures and functions of the two groups of cardiomyocytes differentiated for 15 days are compared in this chapter.

In research of electrophysiological function, according to the present invention, an MEA mapping technology is selected to systematically compare contractility, conductivity and excitability of the hiPS-CMs, excitation conduction, an excitation origin, a propagation direction, a conduction speed and other information of an integral electrical signal of multiple cardiomyocytes are synchronously recorded, and signal tracing of field potential and quantitative analysis of depolarization/repolarization process are carried out on a single cardiomyocyte. It is found that, at the reference line, the hiPS-CMs under optimized induction by the traditional Chinese medicine Compound have a larger beating contraction amplitude, a faster excitation conduction speed and more regular spontaneous beating rhythm. After the hiPS-CMs under optimized induction by the traditional Chinese medicine Compound and standard induction are intervened by applying adrenaline (electric stimulant) or lidocaine (electric inhibitor) at the reference line, the hiPS-CMs under optimized induction by the traditional Chinese medicine Compound have higher sensitivity, stability and tolerance than the hiPS-CMs under standard induction in terms of transmission of integral electrical signal and field potential response of single cell. According to a comprehensive performance of electrophysiological characteristics of the integral and single cardiomyocytes, the hiPS-CMs under optimized induction by the traditional Chinese medicine Compound have more perfect intercellular electrical structure connection and more mature electrophysiological function.

$Ca^{2+}$ is an important ion in the cardiomyocytes, and besides participating in formation of action potential, excitation-contraction coupling mediated by $Ca^{2+}$ is an initial link of contraction beating of the cardiomyocytes. After membrane depolarization of the cardiomyocytes, an L-shaped calcium channel is opened, so that intracellular $Ca^{2+}$ is rapidly released and increased, and a concentration of $Ca^{2+}$ is instantaneously increased to form a temporal and spatial effect, which is the calcium transient. A change of fluorescence intensity detected by the calcium transient reflects contraction intensity of the cardiomyocytes, and time for fluorescence to fall from a peak value to the reference line reflects a diastolic function of the cardiomyocytes. Spontaneous contraction intensity of the hiPS-CMs under optimized induction by the traditional Chinese medicine Compound is higher than that of the standard induction group, it is considered in the present invention that there may be a difference between intracellular calcium transients, and then related indexes of the calcium transient of the hiPS-CMs are detected by a laser scanning confocal microscope in the present invention to evaluate an intracellular calcium circulation state. It is found in the present invention that the hiPS-CMs under optimized induction by the traditional Chinese medicine Compound may complete strong spontaneous contraction once in a basic state only by releasing a small amount of calcium at a contraction frequency higher than that of the standard induction group, which partially explains the reason that contractility of the cardiomyocytes under optimized induction by the traditional Chinese medicine Compound is higher than that of the standard induction group under the same conditions from the perspective of calcium circulation.

In order to maintain regular contraction of the cardiomyocytes, in addition to stable transmission of the electrical signal, sufficient energy supply is also needed. The cardiomyocytes belong to a cell group with most abundant mitochondria in the whole body, and 90% of ATP produced by oxidative phosphorylation of mitochondria is used to ensure energy consumption caused by continuous contraction of the cardiomyocytes. In addition, it has been reported that the mitochondria have a function of regulating myocardial differentiation and embryonic heart development in an embryonic stage to some extent. Therefore, it is considered in the present invention that, since the hiPS-CMs under optimized induction by the traditional Chinese medicine Compound have an obvious advantage in contractility compared with the standard induction group, does the added traditional Chinese medicine Compound in the present invention not only promote electrophysiological development and maturity, but also promote mitochondrial maturation of the hiPS-CMs. Furthermore, according to the present invention, structural and functional detections are carried out on the mitochondria of the hiPS-CMs by an immunofluorescence staining method. Results show that most of the mitochondria in the hiPS-CMs under optimized induction by the traditional Chinese medicine Compound are lines, branches or even reticula, and a mitochondrial matrix is relatively compact, while most of the mitochondria in the hiPS-CMs of the standard induction group are points and particles. It is known in the present invention that mitochondria of mouse embryos are points and small dots and incomplete on a 9.5th day, and the mitochondria start to appear branched, filamentary and reticular structures on a 13.5th day of development. Thus, it can be seen a differentiation and maturation process of the mitochondrial structure of the hiPS-CMs under optimized induction by the traditional Chinese medicine Compound is more similar to a development and maturation process of the mitochondrial structure in the embryonic stage. On a functional level, electrochemical potential energy will be stored in a mitochondrial inner membrane in a respiratory oxidation process of the mitochondria to form the mitochondrial membrane potential, the mitochondrial membrane potential is the premise of ATP production, more energy is produced when the membrane potential is higher, and an important change in an injury and apoptosis process of the cardiomyocytes is collapse of the mitochondrial membrane potential. According to the present invention, intracellular mitochondrial membrane potentials of the hiPS-CMs under optimized induction by the traditional Chinese medicine Compound and standard induction are compared. It is found that the intracellular mitochondrial membrane potential of the hiPS-CMs under optimized induction by the traditional Chinese medicine Compound is slightly higher than that of the standard induction group, but there is no significant difference in quantitative statistics, indicating that there is little difference between energy metabolism abilities of the two groups of hiPS-CMs, and cell states are very good. However, the Compound induction group may have a slight advantage in mitochondrial membrane energy storage. In addition, the mitochondrial calcium is also a key factor to evaluate a mitochondrial function, and a conveying capacity of mitochondrial calcium ions is an important index to measure intensity of heart beating driven by energy produced. Excessive intake of calcium by the mitochondria may lead to calcium accumulation and even calcium overload, which may promote cell aging and death, and many senile degenerative diseases are related to mitochondrial calcium overload in cells. According to the present invention, it is found from quantitative analysis of the mitochondrial calcium of the hiPS-CMs under optimized induction by the traditional Chinese medicine Compound and standard induction that the hiPS-CMs under optimized induction by the traditional Chinese medicine Compound have less calcium accumulation, which shows from a side that homeostasis regulation of intracellular calcium is more excellent, and cell aging and damage are less. On the contrary, if there is cell damage, fragmentation of damaged mitochondria may lead to release of the mitochondrial cytochrome C into the cytoplasm, thus leading to cell apoptosis. By detection of the mitochondrial cytochrome C of the hiPS-CMs under optimized induction by the traditional Chinese medicine Compound and standard induction, no cytochrome C is released into the cytoplasm in the two groups of hiPS-CMs, wherein more mitochondrial cytochrome C of the hiPS-CMs under optimized induction by the traditional Chinese medicine Compound is enriched, indicating that the traditional Chinese medicine compound-assisted induction can not only reduce accumulation of harmful substances, but also play a certain protective role in preventing cell apoptosis.

To sum up, according to the present invention, by adding independently developed traditional Chinese medicine Compound, the hiPS-CMs with a high differentiation rate and high sensitivity are successfully established, which provides an ideal in-vitro experimental model for drug metabolism, toxicity detection and new drug development, and is also an optimal tool for developing etiological research of major and difficult heart diseases in the future. In addition, a stable electrophysiological function and a mature ultra micro-structure of the hiPS-CMs optimally induced by the traditional Chinese medicine Compound have great therapeutic potential in repairing damaged myocardium by in-vivo transplantation treatment, and may provide brand-new therapeutic idea and method for clinical prevention and treatment of chronic heart diseases, thus having broad promotion and application prospects.

Although the implementation of the present invention has been disclosed above, it is not limited to the applications listed in the specification and the embodiments, and can be fully applied to various fields suitable for the present invention, and additional modifications can be easily implemented by those skilled in the art. Therefore, the present invention is not limited to the specific details and illustrations shown and described herein without departing from the general concept defined by the claims and the equivalent scope.

What is claimed is:

1. A traditional Chinese medicine compound with a function of promoting directional differentiation of stem cells into cardiomyocytes, consisting of bulk pharmaceutical chemicals: syngnathus, cornu cervi pantotrichum, hippocampus, ginseng, astragalus, epimedium, placenta hominis, salvia miltiorrhiza, gynostemma pentaphyllum, and saussurea involucrata, in a weight ratio of 1:1:1:1:1:1:1:1:1:1.

2. The traditional Chinese medicine compound with the function of promoting directional differentiation of stem cells into cardiomyocytes according to claim 1, wherein the syngnathus, the cornu cervi pantotrichum, the hippocampus, the ginseng, the astragalus, the epimedium, the placenta hominis, the salvia miltiorrhiza, the gynostemma pentaphyllum, and the saussurea involucrata all in powder form.

3. The traditional Chinese medicine compound with the function of promoting directional differentiation of stem cells into cardiomyocytes according to claim 2, wherein various traditional Chinese medicine powders consisting of a syngnathus powder, a cornu cervi pantotrichum powder, a hippocampus powder, a ginseng powder, an astragalus powder, an epimedium powder, a placenta hominis powder, a salvia miltiorrhiza powder, a gynostemma pentaphyllum powder, and a saussurea involucrata powder are respectively dissolved in Dimethyl Sulfoxide to be prepared into stock solutions for use.

4. A traditional Chinese medicine effective ingredient compound with a function of promoting directional differentiation of stem cells into cardiomyocytes, consisting of ingredients: icariin, astragaloside, ginsenoside Rg1, recombinant human placenta growth factor-2, salvianolic acid B, sphingosine-I-phosphate, velvet antler polypeptide, a syngnathus extract, and a hippocampus extract, wherein the icariin is 20 pg/mL, the astragaloside is 20 pg/mL, the ginsenoside Rgl is 20 pg/mL, the recombinant human placenta growth factor −2 is 5 ng/ml, the salvianolic acid B is 10 pg/mL, the sphingosine-I-phosphate is 2 nM, the velvet antler polypeptide is 100 pg/mL, the syngnathus extract is 100 pg/mL, and the hippocampus extract is 100 pg/mL.

* * * * *